(12) United States Patent
Edgerton et al.

(10) Patent No.: US 10,124,166 B2
(45) Date of Patent: Nov. 13, 2018

(54) NON INVASIVE NEUROMODULATION DEVICE FOR ENABLING RECOVERY OF MOTOR, SENSORY, AUTONOMIC, SEXUAL, VASOMOTOR AND COGNITIVE FUNCTION

(71) Applicant: Neuroenabling Technologies, Inc., Laguna Niguel, CA (US)

(72) Inventors: Victor Reggie Edgerton, Los Angeles, CA (US); Yury P. Gerasimenko, Los Angeles, CA (US); Nicholas A. Terrafranca, Laguna Niguel, CA (US); Daniel C. Lu, Rancho Palos Verdes, CA (US)

(73) Assignee: Neuroenabling Technologies, Inc., Laguna Niguel, CA (US)

( * ) Notice: Subject to any disclaimer, the term of this patent is extended or adjusted under 35 U.S.C. 154(b) by 0 days.

(21) Appl. No.: 15/096,014

(22) Filed: Apr. 11, 2016

(65) Prior Publication Data
US 2016/0220813 A1  Aug. 4, 2016

Related U.S. Application Data

(63) Continuation of application No. 14/357,481, filed as application No. PCT/US2012/064874 on Nov. 13, 2012, now Pat. No. 9,393,409.

(60) Provisional application No. 61/559,025, filed on Nov. 11, 2011.

(51) Int. Cl.
*A61N 1/06* (2006.01)
*A61N 1/36* (2006.01)
*A61N 1/04* (2006.01)

(52) U.S. Cl.
CPC ....... *A61N 1/36003* (2013.01); *A61N 1/0456* (2013.01); *A61N 1/36021* (2013.01); *A61N 1/36025* (2013.01); *A61N 1/36071* (2013.01); *A61N 1/36057* (2013.01);
(Continued)

(58) Field of Classification Search
USPC ..................................................... 607/45–46
See application file for complete search history.

(56) References Cited

U.S. PATENT DOCUMENTS

| | | |
|---|---|---|
| 3,543,761 A | 12/1970 | Bradley |
| 3,662,758 A | 5/1972 | Glover |
| 3,724,467 A | 4/1973 | Avery et al. |

(Continued)

FOREIGN PATENT DOCUMENTS

| | | |
|---|---|---|
| JP | 2002-200178 A | 7/2002 |
| JP | 2008-067917 A | 3/2008 |

(Continued)

OTHER PUBLICATIONS

Ganley et al., Epidural spinal cord stimulation improves locomoter performance in low ASIA C, Wheel-chair-Dependent, spinal cord-injured individuals: Insights from metabolic response. Top. Spinal Cord Inj. Rehabil; 11(2);50-63 (2005).
(Continued)

*Primary Examiner* — Paula J Stice
(74) *Attorney, Agent, or Firm* — K&L Gates LLP; Louis C. Cullman; Dennis A. Majewski

(57) ABSTRACT

In one example embodiment, a neuromodulation system for inducing locomotor activity in a mammal, in cooperation with a signal generator and an electrode, delivers a signal with an overlapping high frequency pulse to a mammal.

20 Claims, 13 Drawing Sheets

(52) U.S. Cl.
CPC ...... *A61N 1/36171* (2013.01); *A61N 1/36175* (2013.01); *A61N 1/36178* (2013.01)

(56) References Cited

U.S. PATENT DOCUMENTS

| | | |
|---|---|---|
| 4,044,774 A | 8/1977 | Corbin et al. |
| 4,102,344 A | 6/1978 | Conway et al. |
| 4,141,365 A | 2/1979 | Fischell et al. |
| 4,285,347 A | 8/1981 | Hess |
| 4,340,063 A | 7/1982 | Maurer |
| 4,379,462 A | 4/1983 | Borkan et al. |
| 4,414,986 A | 11/1983 | Dickhudt et al. |
| 4,538,624 A | 9/1985 | Tarjan |
| 4,549,556 A | 10/1985 | Tajan et al. |
| 4,800,898 A | 1/1989 | Hess |
| 4,934,368 A | 6/1990 | Lynch |
| 5,002,053 A | 3/1991 | Garcia-Rill et al. |
| 5,031,618 A | 7/1991 | Mullett |
| 5,081,989 A | 1/1992 | Graupe |
| 5,121,754 A | 6/1992 | Mullett |
| 5,344,439 A | 9/1994 | Otten |
| 5,354,320 A | 10/1994 | Schaldach |
| 5,374,285 A | 12/1994 | Vaiani et al. |
| 5,417,719 A | 5/1995 | Hull et al. |
| 5,562,718 A | 10/1996 | Palermo |
| 5,643,330 A | 7/1997 | Holsheimer et al. |
| 5,733,322 A | 3/1998 | Starkebaum |
| 5,983,141 A | 11/1999 | Sluijter et al. |
| 6,066,163 A | 5/2000 | John |
| 6,104,957 A | 8/2000 | Alo et al. |
| 6,122,548 A | 9/2000 | Starkebaum et al. |
| 6,308,103 B1 | 10/2001 | Gielen |
| 6,319,241 B1 | 11/2001 | King et al. |
| 6,470,213 B1 | 10/2002 | Alley |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,819,956 B2 | 11/2004 | DiLorenzo |
| 6,839,594 B2 | 1/2005 | Cohen |
| 6,871,099 B1 | 3/2005 | Whitehurst et al. |
| 6,892,098 B2 | 5/2005 | Ayal |
| 6,895,280 B2 | 5/2005 | Meadows |
| 6,895,283 B2 | 5/2005 | Erickson et al. |
| 6,937,891 B2 | 8/2005 | Leinders |
| 6,950,706 B2 | 9/2005 | Rodriguez |
| 6,975,907 B2 | 12/2005 | Zanakis |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng |
| 7,127,287 B2 | 10/2006 | Duncan |
| 7,127,296 B2 | 10/2006 | Bradley |
| 7,127,297 B2 | 10/2006 | Law et al. |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen |
| 7,239,920 B1 | 7/2007 | Thacker et al. |
| 7,251,529 B2 | 7/2007 | Greenwood-Van |
| 7,252,090 B2 | 8/2007 | Goetz |
| 7,313,440 B2 | 12/2007 | Miesel et al. |
| 7,330,760 B2 | 2/2008 | Heruth et al. |
| 7,337,005 B2 | 2/2008 | Kim |
| 7,377,006 B2 | 2/2008 | Kim |
| 7,340,298 B1 | 3/2008 | Barbut |
| 7,415,309 B2 | 8/2008 | McIntyre |
| 7,463,927 B1 | 12/2008 | Chaouat |
| 7,463,928 B2 | 12/2008 | Lee |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt |
| 7,584,000 B2 | 9/2009 | Erickson |
| 7,590,454 B2 | 9/2009 | Garabedian et al. |
| 7,603,178 B2 | 10/2009 | North et al. |
| 7,628,750 B2 | 12/2009 | Cohen |
| 7,660,636 B2 | 2/2010 | Castel et al. |
| 7,697,995 B2 | 4/2010 | Cross et al. |
| 7,729,781 B2 | 6/2010 | Swoyer et al. |
| 7,734,340 B2 | 6/2010 | De Ridder |
| 7,734,351 B2 | 6/2010 | Testerman |
| 7,769,463 B2 | 8/2010 | Katsnelson |
| 7,797,057 B2 | 9/2010 | Harris |
| 7,801,601 B2 | 9/2010 | Maschino et al. |
| 7,813,803 B2 | 10/2010 | Heruth et al. |
| 7,890,182 B2 | 2/2011 | Parramon et al. |
| 7,949,395 B2 | 5/2011 | Kuzma |
| 7,949,403 B2 | 5/2011 | Palermo |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,108,052 B2 | 1/2012 | Boling |
| 8,131,358 B2 | 3/2012 | Moffitt |
| 8,155,750 B2 | 4/2012 | Jaax |
| 8,170,660 B2 | 5/2012 | Dacey |
| 8,190,262 B2 | 5/2012 | Gerber |
| 8,195,304 B2 | 6/2012 | Strother et al. |
| 8,239,038 B2 | 8/2012 | Wolf |
| 8,260,436 B2 | 9/2012 | Gerber et al. |
| 8,311,644 B2 | 11/2012 | Moffitt |
| 8,332,029 B2 | 12/2012 | Glukhovsky et al. |
| 8,346,366 B2 | 1/2013 | Arle |
| 8,352,036 B2 | 1/2013 | Dimarco |
| 8,355,791 B2 | 1/2013 | Moffitt |
| 8,355,797 B2 | 1/2013 | Caparso et al. |
| 8,364,273 B2 | 1/2013 | De Ridder |
| 8,369,961 B2 | 2/2013 | Christman |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishmamur |
| 8,805,542 B2 | 8/2014 | Tai |
| 2002/0055779 A1 | 5/2002 | Andrews |
| 2002/0111661 A1 | 8/2002 | Cross et al. |
| 2003/0032992 A1 | 2/2003 | Thacker |
| 2003/0078633 A1 | 4/2003 | Firlik et al. |
| 2004/0044380 A1 | 3/2004 | Buringa |
| 2004/0122483 A1 | 6/2004 | Nathan et al. |
| 2004/0133248 A1 | 7/2004 | Frei et al. |
| 2004/0138518 A1 | 7/2004 | Rise et al. |
| 2004/0172097 A1 | 9/2004 | Brodard et al. |
| 2004/0181263 A1 | 9/2004 | Blazer et al. |
| 2005/0004622 A1 | 1/2005 | Cullen et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0231186 A1 | 10/2005 | Barrera et al. |
| 2005/0246004 A1 | 11/2005 | Cameron et al. |
| 2006/0041295 A1 | 2/2006 | Osypka |
| 2006/0089696 A1 | 4/2006 | Olsen et al. |
| 2006/0100671 A1 | 5/2006 | Ridder |
| 2006/0122678 A1 | 6/2006 | Olsen et al. |
| 2006/0142822 A1 | 6/2006 | Tulgar |
| 2006/0149337 A1 | 7/2006 | John |
| 2006/0195153 A1 | 8/2006 | DiUbaldi et al. |
| 2006/0239482 A1 | 10/2006 | Hatoum |
| 2006/0241356 A1 | 10/2006 | Flaherty |
| 2007/0016097 A1 | 1/2007 | Farquhar et al. |
| 2007/0049814 A1 | 3/2007 | Muccio |
| 2007/0060954 A1 | 3/2007 | Cameron et al. |
| 2007/0060980 A1 | 3/2007 | Strother et al. |
| 2007/0083240 A1 | 4/2007 | Peterson et al. |
| 2007/0156179 A1 | 7/2007 | S.E. |
| 2007/0179534 A1 | 8/2007 | Firlik et al. |
| 2007/0191709 A1 | 8/2007 | Swanson |
| 2007/0233204 A1 | 10/2007 | Lima et al. |
| 2007/0265691 A1 | 11/2007 | Swanson |

(56) References Cited

U.S. PATENT DOCUMENTS

| | | |
|---|---|---|
| 2008/0009927 A1 | 1/2008 | Vilimis |
| 2008/0046049 A1 | 2/2008 | Skubitz et al. |
| 2008/0051851 A1 | 2/2008 | Lin |
| 2008/0103579 A1 | 5/2008 | Gerber |
| 2008/0140152 A1 | 6/2008 | Imran et al. |
| 2008/0140169 A1 | 6/2008 | Imran |
| 2008/0183224 A1 | 7/2008 | Barolat |
| 2008/0221653 A1 | 9/2008 | Agrawal |
| 2008/0228250 A1 | 9/2008 | Mironer |
| 2008/0234791 A1 | 9/2008 | Arle et al. |
| 2008/0294226 A1 | 11/2008 | Moffitt et al. |
| 2009/0112281 A1 | 4/2009 | Miyazawa et al. |
| 2009/0204173 A1 | 8/2009 | Fang |
| 2009/0270960 A1 | 10/2009 | Zhao et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Naggers |
| 2010/0004715 A1 | 1/2010 | Fahey |
| 2010/0023103 A1 | 1/2010 | Elborno |
| 2010/0125313 A1 | 5/2010 | Lee et al. |
| 2010/0137938 A1 | 6/2010 | Kishawi et al. |
| 2010/0152811 A1 | 6/2010 | Flaherty |
| 2010/0185253 A1 | 7/2010 | Dimarco et al. |
| 2010/0217355 A1 | 8/2010 | Tass et al. |
| 2010/0241191 A1 | 9/2010 | Testerman |
| 2010/0274312 A1* | 10/2010 | Alataris ............ A61N 1/36071 607/46 |
| 2010/0312304 A1 | 12/2010 | York et al. |
| 2011/0034977 A1 | 2/2011 | Janik et al. |
| 2011/0054567 A1 | 3/2011 | Lane |
| 2011/0054568 A1 | 3/2011 | Lane |
| 2011/0077660 A1 | 3/2011 | Janik et al. |
| 2011/0130804 A1 | 6/2011 | Lin et al. |
| 2011/0160810 A1 | 6/2011 | Griffith |
| 2011/0184489 A1 | 7/2011 | Nicolelis et al. |
| 2011/0218590 A1 | 9/2011 | Degiorgio et al. |
| 2011/0218594 A1 | 9/2011 | Doron |
| 2011/0224665 A1 | 9/2011 | Crosby et al. |
| 2011/0224753 A1 | 9/2011 | Palermo |
| 2011/0224757 A1 | 9/2011 | Zdeblick et al. |
| 2011/0237921 A1 | 9/2011 | Askin et al. |
| 2012/0035684 A1 | 2/2012 | Thompson et al. |
| 2012/0059432 A1* | 3/2012 | Emborg ............ A61N 1/36003 607/49 |
| 2012/0071950 A1 | 3/2012 | Archer |
| 2012/0109251 A1 | 5/2012 | Lebedev |
| 2012/0123293 A1 | 5/2012 | Shah et al. |
| 2012/0136408 A1* | 5/2012 | Grill ................. A61N 1/36146 607/45 |
| 2012/0165899 A1 | 6/2012 | Gliner |
| 2012/0172946 A1 | 7/2012 | Altaris et al. |
| 2012/0179222 A1 | 7/2012 | Jaax |
| 2012/0232615 A1 | 9/2012 | Barolat |
| 2012/0277834 A1 | 11/2012 | Mercanzini et al. |
| 2012/0330391 A1 | 12/2012 | Bradley et al. |
| 2013/0030501 A1 | 1/2013 | Feler et al. |
| 2013/0035745 A1* | 2/2013 | Ahmed ................ A61N 1/0452 607/66 |
| 2013/0085361 A1 | 4/2013 | Mercanzini et al. |
| 2013/0096640 A1 | 4/2013 | Possover |
| 2013/0123568 A1 | 5/2013 | Hamilton et al. |
| 2013/0253299 A1 | 9/2013 | Weber |
| 2013/0253611 A1 | 9/2013 | Lee |
| 2014/0163640 A1 | 6/2014 | Edgerton et al. |
| 2014/0180361 A1 | 6/2014 | Burdick |
| 2014/0316484 A1 | 10/2014 | Edgerton |
| 2014/0316503 A1 | 10/2014 | Tai |
| 2015/0217120 A1 | 8/2015 | Nandra et al. |
| 2015/0231396 A1 | 8/2015 | Burdick et al. |
| 2016/0030748 A1 | 2/2016 | Edgerton et al. |
| 2016/0121109 A1 | 5/2016 | Edgerton et al. |
| 2016/0175586 A1 | 6/2016 | Edgerton et al. |
| 2016/0310739 A1 | 10/2016 | Burdick et al. |
| 2017/0157389 A1 | 6/2017 | Tai et al. |

FOREIGN PATENT DOCUMENTS

| | | |
|---|---|---|
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2001102533 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| WO | 1997/047357 A1 | 12/1997 |
| WO | 2003/026735 A2 | 4/2003 |
| WO | 2003/092795 A1 | 11/2003 |
| WO | 2004/087116 A2 | 10/2004 |
| WO | 2005/051306 A2 | 6/2005 |
| WO | 2005/087307 A2 | 9/2005 |
| WO | 2007-081764 A2 | 7/2007 |
| WO | 2007/107831 A2 | 9/2007 |
| WO | 2008/070807 A3 | 6/2008 |
| WO | 2008/109862 A2 | 9/2008 |
| WO | 2008/121891 A1 | 10/2008 |
| WO | 2009/042217 A1 | 4/2009 |
| WO | 2009/111142 A2 | 9/2009 |
| WO | 2010/114998 A1 | 10/2010 |
| WO | 2010/124128 A1 | 10/2010 |
| WO | 2011/005607 A1 | 1/2011 |
| WO | 2012/094346 A2 | 7/2012 |
| WO | 2012/100260 A2 | 7/2012 |
| WO | 2012/129574 A2 | 9/2012 |
| WO | 2013/071307 A1 | 5/2013 |
| WO | 2013/071309 A1 | 5/2013 |
| WO | 2014/144785 A1 | 9/2014 |
| WO | 2015/106286 A1 | 7/2015 |

OTHER PUBLICATIONS

"Hermann et al., Spinal Cord stimulation facilitates functional walking in a chronic, incomplete spinal cord injured. Spinal Cord, vol. 40, pp. 65-68 (2002).".

International Search Report for International Application Serial No. PCT/US2012/020112 filed on Jan. 3, 2012.

International Search Report for International Application Serial No. PCT/US2012/022257 filed on Jan. 23, 2012.

International Search Report for International Application Serial No. PCT/US2012/030624 filed on Mar. 26, 2012.

International Search Report for International Application Serial No. PCT/US2014/029340 filed on Mar. 14, 2014.

Nandra et al., A parylene-based microelectrode arrary implant for spinal cord stimulation in rats. Conf. Proc. IEEE Eng. Med. Biol. Soc., pp. 1007-1010 (2011).

Nandra et al., A wireless microelectode implant for spinal cord stimulation and recording in rats. Presentation Abstract, 2013.

Transcutaneous Lumbar Spinal Cord Stimulation, http://www.restrorativeneurology.org (available online and attached), International Society for Restorative Neurology, 2012.

Rodger et al., High density flexible parylene-based multielectrode arrays for retinal and spinal cord stimulation. Proc. of the 14th International Conference on Solid-State Sensors, Actuators and Microsystems, pp. 1385-1888 (2007).

International Search Report for International Application Serial No. PCT/US2012/064874 filed on Nov. 13, 2012.

International Search Report for International Application Serial No. PCT/US2012/064878 filed on Nov. 13, 2012.

Dimitrijevic et al., Clinical elements for the neuromuscular stimulation and functional electrical stimulation protocols in the practice of neurorehabilitation, Artificial Organs, 26(3): 256-259 (2002).

(56) References Cited

OTHER PUBLICATIONS

Dimitrijevic et al., Evidence for a spinal central pattern generator in humans. Annals New York Academy Sciences, 860: 360-376 (1998).
Gerasimenko et al., Control of locomotor activity in humans and animals in the absence of supraspinal influences. Neuroscience and Behavioral Physiology, 32(4): 417-423 (2002).
Hofstoetter et al., Modification of reflex responses to lumbar posterior root stimulation by motor tasks in healthy subjects. Artificial Organs, 32(8):644-648 (2008).
Hofstoetter et al., Model of spinal cord reflex circuits in humans: stimulation frequency-dependence of segmental activities and their interactions. Second Congress International Society of Intraoperative Neurophysiology (ISIN), Dubrovnik, Croatia, pp. 8-10 (2009).
International Search Report and Written Opinion dated May 19, 2015 for International Application Serial No. PCT/US2015/011263 filed on Jan. 13, 2015.
Jilge et al, Initiating extension of the lower limbs in subjects with complete spinal cord injury by epidural lumbar cord stimulation. Exp Brain Res., 154: 308-326 (2004).
Ladenbauer et al., Stimulation of the human lumbar spinal cord with implanted and surface electrodes: a computer simulation study. IEEE Transactions on Neural Systems and Rehabilitation Engineering, 18(6):637-645 (2010).
Minassian et al., Transcutaneous stimulation of the human lumbar spinal cord: Facilitating locomotor output in spinal cord injury. Society for Neuroscience, Conference Proceedings, Neuroscience 2010, San Diego, CA, Abstract Viewer/Itinerary Planner No. 286.19, Abstract & Poster attached (2010).
Minassian et al., Human lumbar cord circuitries can be activated by extrinsic tonic input to generate locomotor-like activity. Human Movement Science, 26(2):275-295 (2007).
Minassian et al., Posterior root-muscle reflexes elicited by transcutaneous stimulation of the human lumbosacral cord. Muscle & Nerve, 35(3):327-336 (2007) Article first published online in 2006.
Minassian et al., Stepping-like movements in humans with complete spinal cord injury induced by epidural stimulation of the lumbar cord: electromyographic study of compound muscle action potentials. Spinal Cord, 42: 401-416 (2004).
Minassian et al., Peripheral and central afferent input to the lumbar cord. Biocybernetics and Biomedical Engineering, 25(3): 11-29 (2005).
Minassian et al., Human lumbar cord model of the locomotor central pattern generator. Second Congress International Society of Intraoperative Neurophysiology (ISIN), Dubrovnik, Croatia, pp. 11-13 (2009).
Minassian et al., Posterior root-muscle reflex, Second Congress International Society of Intraoperative Neurophysiology (ISIN), Dubrovnik, Croatia, pp. 77-80 (2009).
Murg et al., Epidural electric stimulation of posterior structures of the human lumbar spinal cord: 1. Muscle twitches—a functional method to define the site of stimulation. Spinal Cord, 38: 394-402 (2000).
Rattay et al., Epidural electrical stimulation of posterior structures of the human lumbosacral cord: 2. Quantitative analysis by computer modeling. Spinal Cord, 38: 473-489 (2000).

Supplementary European Search Report and Opinion for European Patent Application Serial No. 12848368.2 filed on Nov. 13, 2012.
Ward, Electrical Stimulation Using Kilohertz-Frequency Alternating Current. Physical therapy, 89:181-190 (2009) (published online Dec. 18, 2008).
Gerasimenko et al., Noninvasive reactivation of motor descending control after paralysis. Journal of Neurotrauma, 2015 (article has been peer-reviewed and accpeted for publication, 49 pages).
Danner et al., Body position influences which neural structures are recruited by lumbar transcutaneous spinal cord stimulation. PLoS ONE 11(1):e0147479 (2016).
Dimitrijevic et al., Electrophysiological characteristics of H-reflexes elicited by percutaneous stimulation of the cauda equina. Abstract No. 4927, 34th Annual Meeting of the Society for Neuroscience, San Diego, CA (2004).
Hofstoetter et al., Modification of spasticity by transcutaneous spinal cord stimulation in individuals with incomplete spinal cord injury. The Journal of Spinal Cord Medicine, 37:2, 202-211 (2014).
Hofstoetter et al., Effects of transcutaneous spinal cord stimulation on voluntary locomotor activity in an incomplete spinal cord injured individual. Biomed Tech, 58 (Suppl. 1) 2013.
Krenn et al., Selectivity of transcutaneous stimulation of lumbar posterior roots at different spinal levels in humans. Biomed Tech, 58 (Suppl. 1) (2013).
Minassian et al., Neurophysiology of the human lumbar locomotor pattern generator. 2010. 15th Annual Conference of the International Functional Electrical Stimulation Society. Annual IFESS Conference Proceedings.
Minassian et al., Mechanisms of rhythm generation of the human lumbar spinal cord in repose to tonic stimulation without and with step-related sensory feedback. Biomed Tech, 58 (Suppl. 1) (2013).
Minassian et al., Neuromodulation of lower limb motor control in restorative neurology. Clinical Neurology and Neurosurgery, 114:489-497 (2012).
Rasmussen, Carl Edward. Gaussian Processes in Machine Learning. Machine Learning, L.N.A.I. 3176, p. 63-71 (2003).
Office Action for Canadian Patent Application No. 2,824,782 dated Nov. 29, 2017.
Office Action for Australian Patent Application No. 2017221868 dated Jan. 23, 2018.
Office Action for Canadian Patent Application No. 2,825,550 dated Jan. 24, 2018.
U.S. Office Action for U.S. Appl. No. 14/925,791 dated Jul. 20, 2017.
Office Action for European Patent Application No. 12760696.0 dated Nov. 9, 2017.
Office Action for Canadian Patent Application No. 2,823,592 dated Oct. 5, 2017.
Office Action for Australian Patent Application No. 2017203132 dated Oct. 13, 2017.
Examination Report for Australian Patent Application No. 2017202237 dated Apr. 6, 2018.
Office Action for Canadian Patent Application No. 2,856,202 dated Jun. 19, 2018.
Office Action for European Patent Application No. 12848368.2 dated May 9, 2018.

\* cited by examiner

NON INVASIVE NEUROMODULATION DEVICE FOR ENABLING RECOVERY OF MOTOR, SENSORY, AUTONOMIC, SEXUAL, VASOMOTOR AND COGNITIVE FUNCTION

CROSS REFERENCES TO RELATED APPLICATIONS

The present application is a continuation of U.S. patent application Ser. No. 14/357,481, filed May 9, 2014, now U.S. Pat. No. 9,393,409, which is a national phase filing of International Patent Application No. PCT US2012/064874, filed Nov. 13, 2012, which claims priority to U.S. Provisional Patent Application No. 61/559,025, filed in the United States Patent Office on Nov. 11, 2011, the entire contents of which is being incorporated herein by reference.

BACKGROUND

Serious spinal cord injuries (SCI) affect approximately 1.3 million people in the United States, and roughly 12-15,000 new injuries occur each year. Of these injuries, approximately 50% are complete spinal cord injuries in which there is essentially total loss of sensory motor function below the level of the spinal lesion.

Neuronal networks formed by the interneurons of the spinal cord that are located in the cervical and lumbar enlargements, such as the spinal networks (SNs), play an important role in the control of posture, locomotion and movements of the upper limbs, breathing, swallowing and speech. Most researchers believe that all mammals, including humans, have SNs in the lunbosacral cord. See Dimitrijevic, M. R, Gerasimenko, Yu., and Pinter, M. M., Evidence for a Spinal Central Pattern Generator in Humans, Ann. N. Y. Acad. Sci., 1998, vol. 860, p. 360; Gurfinkel', V. S., Levik, Yu. S., Kazennikov, O. V., and Selionov, V. A., Does the Prime Mover of Stepping Movements Exist in Humans?, Human Physiology, 1998, vol. 24, no. 3, p. 42; Gerasimenko, Yu. P., Roy, R. R., and Edgerton, V R., Epidural Stimulation: Comparison of the Spinal Circuits That Generate and Control Locomotion in Rats, Cats and Humans, Exp. Neurol., 2008, vol. 209, p. 417. Normally, the activity of SNs is regulated supraspinally and by peripheral sensory input. In the case of disorders of the connections between the brain and spinal cord, e.g., as a result of traumatic spinal cord lesions, motor tasks can be enabled by epidural electrical stimulation of the lumbosacral and cervicalsegments as well as the brainstem. It has been shown that epidural electrical spinal cord stimulation (eESCS) with enough intensity can induce electromyographic (EMG) patterns in the leg muscles of patients with clinically complete spinal cord injury. See Dimitrijevic, Gerasimenko, Yu., and Pinter, supra; Minassian, K., Persy, I., Rattay, F, Pinter, M. M., Kern, H., and Dimitrijevic, M. R., Human Lumbar Cord Circuitries Can Be Activated by Extrinsic Tonic Input to Generate Locomotor-Like Activity, Human 1Hovement Sci., 2007, vol. 26, p. 275. But the novelty of the approach described in this document is that the spinal circuitry can be neuromodulated to a physiological state that facilitates or enables the recovery or improved control of movement without actually inducing the movement following some neuromotor dysfunction. Harkema, S., Gerasimenko, Y, Hodes, J., Burdick, J., Angeli, e., Chen, Y, Ferreira, e., Willhite, A., Rejc, E., Grossman, R. G., and Edgerton, V R., Epidural Stimulation of the Lumbosacral Spinal Cord Enables Voluntary Movement, Standing, and Assisted Stepping in a Paraplegic Human, Lancet, 2011, vol. 377, p. 1938.

eESCS is an invasive method and requires surgical implantation of electrodes on the dorsal surface of the spinal cord, which limits this method of activating SNs to clinics.

Recently, noninvasive methods for activating the SNs by means of leg muscle vibration and spinal cord electromagnetic stimulation was suggested. It was found that the vibration of the tendons of the hip muscles initiates involuntary walking movements in subjects lying on their side with an external support for the legs. See Gurfinkel', V S., Levik, Yu. S., Kazennikov, O. V, and Selionov, V A., Locomotor-Like Movements Evoked by Leg Muscle Vibration in Humans, Eur. J lVeurosci., 1998, vol. 10, p. 1608; Selionov, V A., Ivanenko, Yu. P., Solopova, 1 A., and Gurfinkel', VS., Tonic Central and Sensory Stimuli Facilitate Involuntary Air-Stepping in Humans, J Neurophysiol., 2009, vol. 101, p. 2847. In addition, electromagnetic stimulation of the rostral segments of the lumbar spinal cord caused involuntary walking movements in healthy subjects in a similar position with a support for the legs. See Gerasimenko, Yu., Gorodnichev, R., Machueva, E., Pivovarova, E., Semenov, D., Savochin, A., Roy, R. R., and Edgerton, V R., Novel and Direct Access to the Human Locomotor Spinal Circuitry, J New'osci., 2010, vol. 30, p. 3700; Gorodnichev, R. M., Machueva, E. M., Pivovarova, E. A., Semenov, D. V, Ivanov, S. M., Savokhin, A. A., Edgerton, V R., and Gerasimenko, Yu. P., A New Method for the Activation of the Locomotor Circuitry in Humans, Hum. Physiol., 2010, vol. 36, no. 6, p. 700. Step-like movements elicited by vibration and electromagnetic stimulation, have apparently a different origin. In the former case, the SN is activated by afferent input mainly due to the activation of muscle receptors, whereas in the latter case, the neuronal locomotor network is affected directly. Each of these methods has its specificity. For example, the vibratory muscle stimulation elicits involuntary locomotor movements only in the hip and knee joints, without the involvement of the ankle. In addition, these characteristic movements could be evoked only in 50% of the subjects. See Selionov, Ivanenko, Solopova, and Gurfinkel', supra. The percentage of subjects in whom the spinal cord electromagnetic stimulation evoked involuntary step like movements was even smaller (10%), although in this case, the kinematic structure of the resultant movements was consistent with the natural random step-like movements to a greater extent than in the case of vibration. See Gerasimenko, Gorodnichev, Machueva, Pivovarova, Semenov, Savochin, Roy, and Edgerton, supra; Gorodnichev, Machueva, Pivovarova, Semenov, Ivanov, Savokhin, Edgerton, and Gerasimenko, supra. In addition, spinal cord electromagnetic stimulation is limited by the technical capabilities of the stimulator. The modem magnetic stimulator used in clinics (e.g., Magstim Rapid) can provide only short-exposure stimulating effects. The electromagnetic stimulator, with the parameters required to elicit step-like movements (5 Hz and 1.5 T), could be sustained for only 15 s.

Accordingly, a need exists for the further development of neuromodulation systems and devices.

SUMMARY

In some embodiments, the neuromodulation system is used with a mammal (e.g., a human) having a spinal cord with at least one selected dysfunctional spinal circuit or other neurologically derived source of control of movement in a portion of the subject's body. Transcutaneous electrical spinal cord stimulation (tESCS) applied in the region of the T11-T12 vertebrae with a frequency of 5-40 Hz may elicit involuntary step-like movements in healthy subjects with their legs suspended in a gravity-neutral position. Amplitude of evoked step-like movements may increase with increasing tESCS frequency. Frequency of evoked step-like movements may not depend on the frequency of tESCS. It was shown that the hip, knee, and ankle joints were involved in the evoked movements. In conclusion, transcutaneous electrical spinal cord stimulation (tESCS) can be used as a noninvasive method in rehabilitation of spinal pathology. By way of non-limiting examples, application of transcutaneous electrical spinal cord stimulation (tESCS) activates spinal networks (SNs), in part via the dorsal roots and the gray matter of the spinal cord. When activated, the SNs may (a) enable voluntary movement of muscles involved in at least one of standing, stepping, reaching, grasping, voluntarily changing positions of one or both legs, breathing, swallowing, speech control, voiding the patient's bladder, voiding the patient's bowel, postural activity, and locomotor activity; (b) enable or improve autonomic control of at least one of cardiovascular function, body temperature, and metabolic processes; (c) help facilitate recovery of at least one of an autonomic function, sexual function, vasomotor function, and cognitive function; and/or (d) help to resolve and/or block pain and spasm.

The paralysis may be a motor complete paralysis or a motor incomplete paralysis. The paralysis may have been caused by a spinal cord injury classified as motor complete or motor incomplete. The paralysis may have been caused by an ischemic or traumatic brain injury. The paralysis may have been caused by an ischemic brain injury that resulted from a stroke or acute trauma. By way of another example, the paralysis may have been caused by a neurodegenerative brain injury. The neurodegenerative brain injury may be associated with at least one of Parkinson's disease, Huntington's disease, Alzheimer's, dystonia, ischemia, stroke, amyotrophic lateral sclerosis (ALS), primary lateral sclerosis (PLS), and cerebral palsy.

In one example embodiment, a neuromodulation system is configured to apply electrical stimulation to a portion of a spinal cord of the subject. The electrical stimulation may be applied by at least one active of surface electrode that is applied to the skin surface of the subject. Such an electrode may be positioned at, at least one of a thoracic region, a cervical region, a lumbosacral region of the spinal cord and/or the brainstem. Electrical stimulation may be delivered at 1-40 Hz at 1-200 mA. The electrical stimulation may include at least one of tonic stimulation and intermittent stimulation. The electrical stimulation may include simultaneous or sequential stimulation of different regions of the spinal cord.

In one example embodiment, where the paralysis was caused by a spinal cord injury at a first location along the spinal cord, the electrical stimulation may be applied by an electrode that is on the spinal cord of the patient at a second location below the first location along the spinal cord relative to the patient's brain.

In one example embodiment, a method may include administering one or more neuropharmaceutical agents to the patient. The neuropharmaceutical agents may include at least one of a serotonergic drug, a dopaminergic drug, a noradrenergic drug, a GABAergic drug, and glycinergic drugs. By way of non-limiting examples, the neuropharmaceutical agents may include at least one of 8-OHDPAT, Way 100.635, Quipazine, Ketanserin, SR 57227A, Ondanesetron, SB 269970, Buspirone, Methoxamine, Prazosin, Clonidine, Yohimbine, SKF-81297, SCH-23390, Quinpirole, and Eticlopride.

The electrical stimulation may be defined by a set of parameter values, and activation of the selected spinal circuit may generate a quantifiable result. In one example embodiment, the neuromodulation system is configured to repeat and use electrical stimulation having different sets of parameter values to obtain quantifiable results generated by each repetition. Thereafter, a machine learning method may be executed by at least one computing device. The machine learning method builds a model of a relationship between the electrical stimulation applied to the spinal cord and the quantifiable results generated by activation of the at least one spinal circuit. A new set of parameters may be selected based on the model. By way of a non-limiting example, the machine learning method may implement a Gaussian Process Optimization.

In one example embodiment, the neuromodulation system is configured to enable at least one function selected from a group consisting of postural and/or locomotor activity, voluntary movement of leg position, when not bearing weight, improved ventilation, swallowing, speech control, voluntary voiding of the bladder and/or bowel, return of sexual function, autonomic control of cardiovascular function, body temperature control, and normalized metabolic processes, in a human subject having a neurologically derived paralysis. The method includes stimulating the spinal cord of the subject using a surface electrode and may include simultaneously subjecting the subject to physical training that exposes the subject to relevant postural proprioceptive signals, locomotor proprioceptive signals, and supraspinal signals while being stimulated with tESCS. At least one of the stimulation and physical training modulates, provokes or incites in real time the electrophysiological properties of spinal circuits in the subject so the spinal circuits are activated by at least one of supraspinal information and proprioceptive information derived from the region of the subject where the selected one or more functions are facilitated.

The region where the selected one or more functions are facilitated may include one or more regions of the spinal cord that control: (a) lower limbs; (b) upper limbs and brainstem for controlling speech; (c) the subject's bladder; and/or (d) the subject's bowel and/or other end organ. The physical training may include standing, stepping, sitting down, lying down, reaching, grasping, stabilizing sitting posture, stabilizing standing posture, practicing speech, swallowing, chewing, deep breathing and coughing.

The surface electrode may include an array of one or more electrodes stimulated in a monopolar biphasic configuration. Such a surface electrode may be placed over at least one of a lumbar, a lumbosacral or sacral portion of the spinal cord, a thoracic portion of the spinal cord, a cervical portion of the spinal cord and/or the brainstem.

The stimulation may include continuous stimulation and/or intermittent stimulation. The stimulation may include simultaneous or sequential stimulation of different spinal cord regions. Optionally, the stimulation pattern may be under control of the subject.

The physical training may include inducing a load bearing positional change in the region of the subject where locomotor activity is to be facilitated. The load bearing positional change in the subject may include standing, stepping, reaching, and/or grasping. The physical training may include robotically guided training.

The method may also include administering one or more neuropharmaceuticals. The neuropharmaceuticals may include at least one of a serotonergic drug, a dopaminergic drug, a noradrenergic drug, a GABAergic drug, and a glycinergic drug.

In one example embodiment, a method includes placing an electrode on the patient's spinal cord, positioning the patient in a training device configured to assist with physical training that is configured to induce neurological signals derived from the portion of the patient's body having motor dysfunction, and applying electrical stimulation to a portion of a spinal cord of the patient.

Another exemplary embodiment is a system that includes a training device configured to assist with physically training of the patient, a surface electrode array configured to be applied on the patient's spinal cord, and a stimulation generator connected to the electrode. When undertaken, the physical training induces neurological signals derived from the portion of the patient's body having the motor dysfunction. The stimulation generator is configured to apply electrical stimulation to the electrode.

Additional features and advantages are described herein, and will be apparent from the following Detailed Description and figures.

BRIEF DESCRIPTION OF THE FIGURES

FIG. 2A: Subject R: the cinematogramms of the joint movements of the right leg and the EMGs of the hip muscles of the right and left legs are shown. Under the EMG, there is a mark of the stimulus. At the right of the cinematogram and EMGs, there are vertical marks of the amplitude in angle degrees and mV, respectively. The duration of records is 40 s. FIG. 2B: Subject S: the EMGs of the hip and ankle muscles of the right leg and the goniograms of the knee joints of the right and left legs; the arrows at the top show the beginning and end of stimulation; the horizontal and vertical labels next to EMG, 10 s and 0.5 mV, respectively; the vertical mark to the right of the goniograms, 200 m V. H, hip; Kn, knee; Ank, ankle; RF, m. rectus femoris; BF, m. biceps femoris; T A, m. tibialis anterior; M G, m. gastrocnemius; (r), on the right; (l), on the left.

DETAILED DESCRIPTION

The present disclosure relates in general to the field of neurological treatment and rehabilitation for injury and disease including traumatic spinal cord injury, non-traumatic spinal cord injury, stroke, movement disorders, brain injury, and other diseases or injuries that result in paralysis and/or nervous system disorder. Systems and devices are provided to facilitate recovery of posture, locomotion, and voluntary movements of the arms, trunk, and legs, and recovery of autonomic, sexual, vasomotor, speech, swallowing, chewing, respiratory and cognitive function, in a human subject having spinal cord injury, brain injury, or any other neurological disorder.

Figure 1:
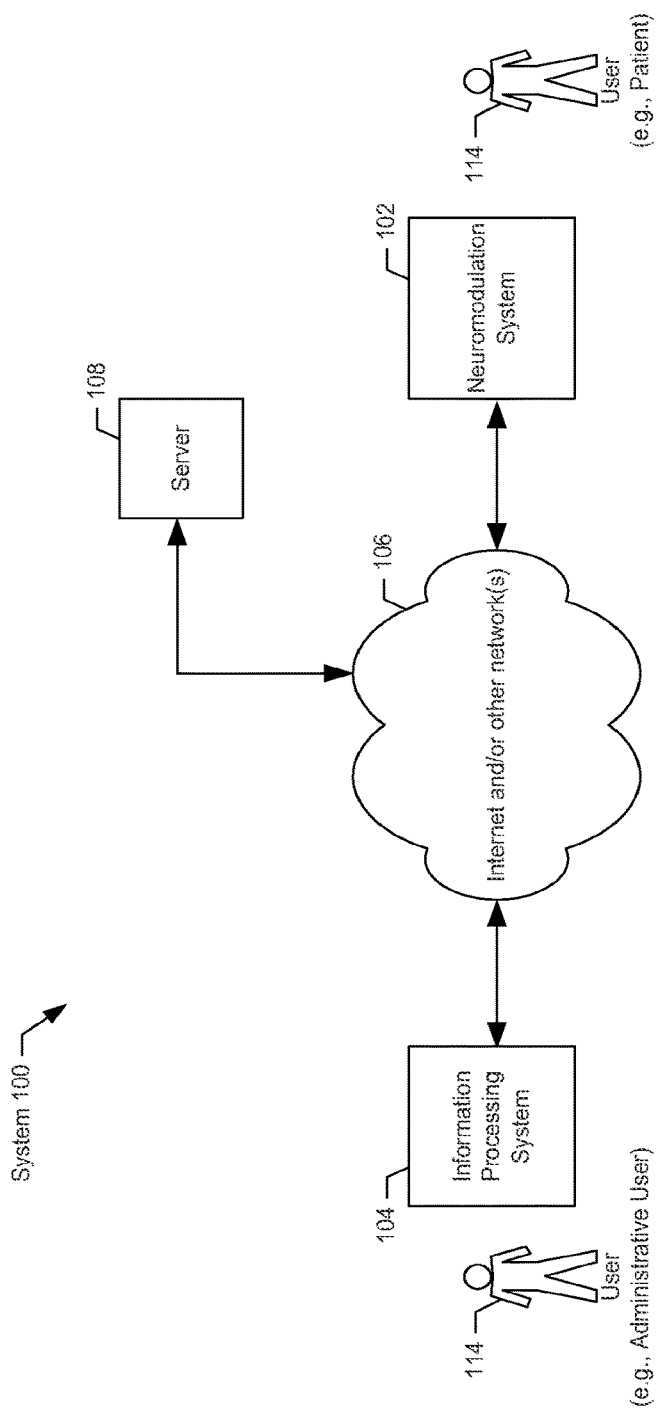
FIG. 1 is a high level block diagram of an example network communicating system, according to an example embodiment of the system disclosed herein.

The present system may be readily realized in a network communications system. A high level block diagram of an example network communications system 100 ("system 100") is illustrated in FIG. 1. In this example, system 100 includes neuromodulation system 102 and information processing system 104.

Information processing system 104 may include a variety of devices, such as desktop computers which typically include a user display for providing information to users and various interface elements as will be discussed in further detail below. Information processing system 104 may include a cellular phone, a personal digital assistant, a laptop computer, a tablet computer, or a smart phone. In some example embodiments, information processing system 104 may include any mobile digital device such as Apple Inc.'s iPhone™, iPod Touch™ and iPad™. Further, information processing system 104 may include smart phones based on Google Inc.'s Android™, Nokia Corporation's Symbian™ or Microsoft Corporation's Windows Mobile™ operating systems or Research In Motion Limited's Blackberry™ etc.

In these embodiments, information processing system 104 is preferably configured to download, install and execute various application programs.

Information processing system 104 may communicate with neuromodulation system 102 via a connection to one or more communications channels 106 such as the Internet or some other data network, including, but not limited to, any suitable wide area network or local area network. It should be appreciated that any of the devices and systems described herein may be directly connected to each other instead of over a network. At least one server 108 may be part of network communications system 100, and may communicate with neuromodulation system 102 and information processing system 104.

Information processing system 104 may interact with a large number of users at a plurality of different neuromodulation systems 102. Accordingly, information processing system 104 may be a high end computer with a large storage capacity, one or more fast microprocessors, and one or more high speed network connections. Conversely, relative to an example high end information processing system 104, each neuromodulation system 102 may include less storage capacity, a single microprocessor, and a single network connection.

It should be appreciated that users as described herein may include any person or entity which uses the presently disclosed system and may include a wide variety of parties. For example, the users described herein may refer to various different entities, including patients, physicians, administrative users, mobile device users, private individuals, and/or commercial partners. It should also be appreciated that although the user in this specification is often described as a patient, the patient may be instead any of the users described herein.

Neuromodulation system 102 and/or servers 108 may store files, programs, databases, and/or web pages in memories for use by information processing system 104, and/or other information processing systems 104 or servers 108.

Neuromodulation system 102 and/or server 108 may be configured according to its particular operating system, applications, memory, hardware, etc., and may provide various options for managing the execution of the programs and applications, as well as various administrative tasks. Information processing system 104 and/or server 108 may interact via at least one network with at least one other information processing system 104 and/or server 108, which may be operated independently. Information processing systems 104 and servers 108 operated by separate and distinct entities may interact together according to some agreed upon protocol.

Figure 2:
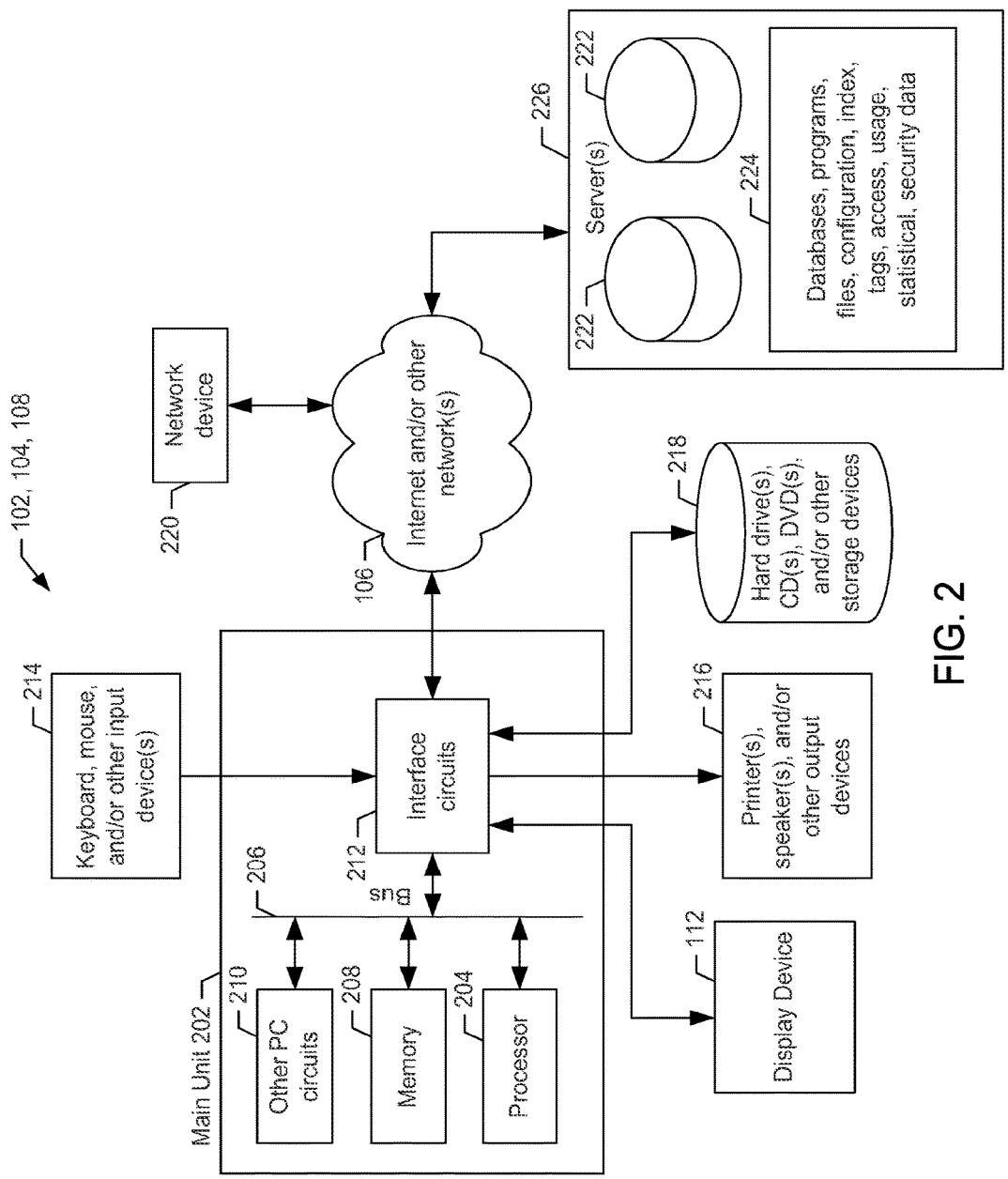
FIG. 2 is a detailed block diagram showing an example of a computing device, according to an example embodiment of the system disclosed herein.

A detailed block diagram of the electrical systems of an example computing device is illustrated in FIG. 2. The example computing device may include any of the devices and systems described herein, including neuromodulation system 102, information processing system 104 and server 108. In this example, the example computing devices may include main unit 202 which preferably includes at least one processor 204 electrically connected by address/data bus 206 to at least one memory device 208, other computer circuitry 210, and at least one interface circuit 212. Processor 204 may be any suitable processor, such as a microprocessor from the INTEL® PENTIUM® family of microprocessors. Processor 204 may include one or more microprocessors, central processing units (CPUs), computing devices, microcontrollers, digital signal processors, or like devices or any combination thereof. Memory 208 preferably includes volatile memory and non-volatile memory.

Preferably, memory 208 stores software program(s) that interact with the other devices in system 100 as described below. This program may be executed by processor 204 in any suitable manner. In an example embodiment, memory 208 may be part of a "cloud" such that cloud computing may be utilized by neuromodulation system 102, information processing system 104 and server 108. Memory 208 may also store digital data indicative of documents, files, programs, web pages, etc. retrieved from computing devices 102, 103 and 104 and/or loaded via input device 214.

Interface circuit 212 may be implemented using any suitable interface standard, such as an Ethernet interface and/or a Universal Serial Bus (USB) interface. At least one input device 214 may be connected to interface circuit 212 for entering data and commands into main unit 202. For example, input device 214 may be at least one of a keyboard, mouse, touch screen, track pad, track ball, isopoint, image sensor, character recognition, barcode scanner, and a voice recognition system.

As illustrated in FIG. 2, at least one display device 112, printers, speakers, and/or other output devices 216 may also be connected to main unit 202 via interface circuit 212. Display device 112 may be a cathode ray tube (CRTs), a liquid crystal display (LCD), or any other suitable type of display device. Display device 112 may be configured to generate visual displays during operation of neuromodulation system 102, information processing system 102 and/or server 108. A user interface may include prompts for human input from user 114 including links, buttons, tabs, checkboxes, thumbnails, text fields, drop down boxes, etc., and may provide various outputs in response to the user inputs, such as text, still images, videos, audio, and animations.

At least one storage device 218 may also be connected to main device or unit 202 via interface circuit 212. At least one storage device 218 may include at least one of a hard drive, CD drive, DVD drive, and other storage devices. At least one storage device 218 may store any type of data, such content data, statistical data, historical data, databases, programs, files, libraries, pricing data and/or other data, etc., which may be used by neuromodulation system 102, information processing system 104 and/or server 108.

Neuromodulation system 102, information processing system 104 and/or server 108 may also exchange data with other network devices 220 via a connection to network 106. Network devices 220 may include at least one server 226, which may be used to store certain types of data, and particularly large volumes of data which may be stored in at least one data repository 222. Server 226 may include any kind of data 224 including user data, application program data, content data, statistical data, historical data, databases, programs, files, libraries, pricing data and/or other data, etc. Server 226 may store and operate various applications relating to receiving, transmitting, processing, and storing the large volumes of data. It should be appreciated that various configurations of at least one server 226 may be used to support and maintain system 100. In some example embodiments, server 226 is operated by various different entities, including private individuals, administrative users and/or commercial partners. Also, certain data may be stored in neuromodulation system 102, information processing system 104 and/or server 108 which is also stored on server 226, either temporarily or permanently, for example in memory 208 or storage device 218. The network connection may be any type of network connection, such as an Ethernet connection, digital subscriber line (DSL), telephone line, coaxial cable, wireless connection, etc.

Access to neuromodulation system 102, information processing system 104 and/or server 108 can be controlled by appropriate security software or security measures. A user's access can be defined by neuromodulation system 102, information processing system 104 and/or server 108 and be limited to certain data and/or actions. Accordingly, users of system 100 may be required to register with neuromodulation system 102, information processing system 104 and/or server 108.

As noted previously, various options for managing data located within neuromodulation system 102, information processing system 104 and/or server 108 and/or in server 226 may be implemented. A management system may manage security of data and accomplish various tasks such as facilitating a data backup process. The management system may update, store, and back up data locally and/or remotely. A management system may remotely store data using any suitable method of data transmission, such as via the Internet and/or other networks 106.

Figure 3:
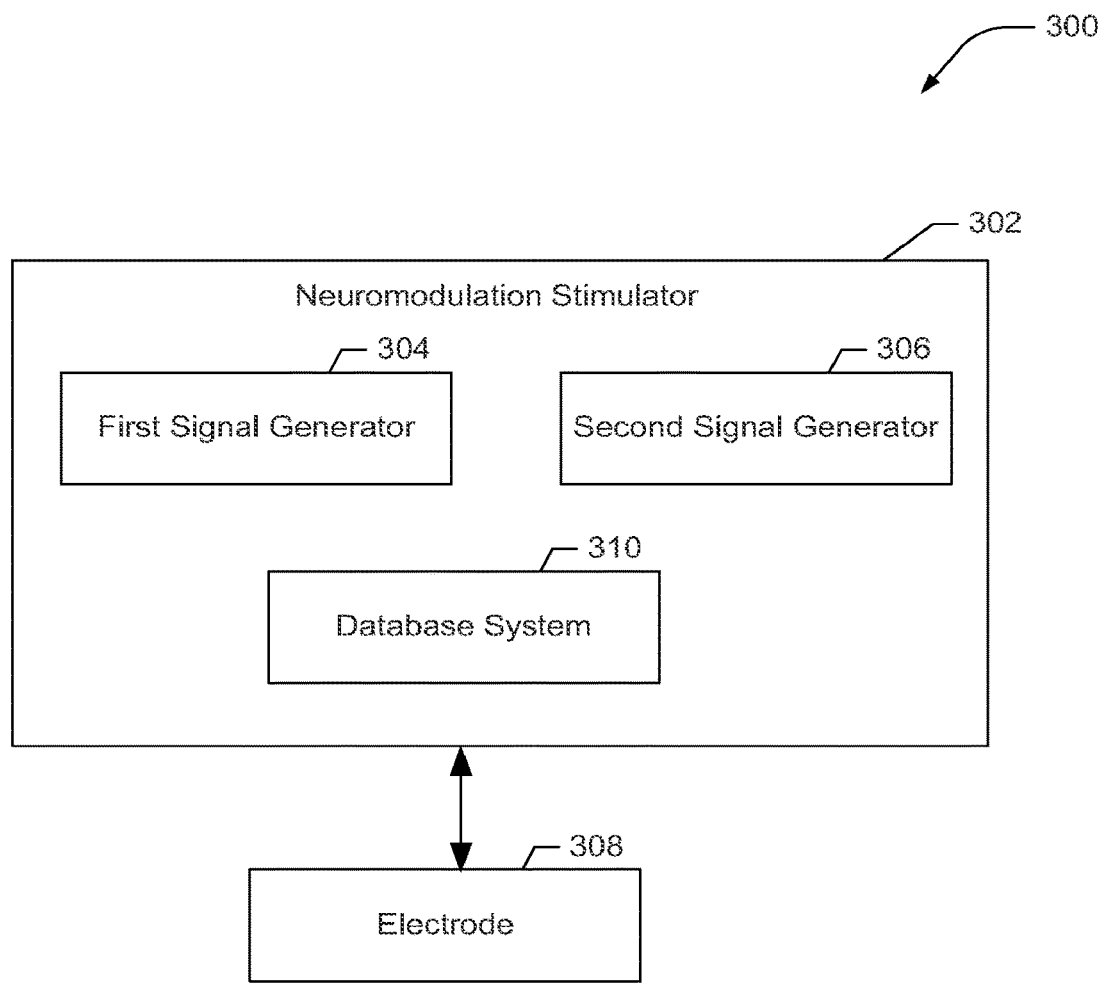
FIG. 3 is a block diagram of an example neuromodulation system in accordance with one example embodiment of the system disclosed herein.

FIG. 3 is a block diagram showing an example neuromodulation system 300. It should be appreciated that neuromodulation system 300 illustrated in FIG. 3 may be implemented as neuromodulation system 102.

As illustrated in FIG. 3, in this example, neuromodulation system 300 may include neuromodulation stimulator device 302 which is operatively connected to at least one electrode 308. Neuromodulation stimulator device 302 may be connected to at least one electrode 308 in any suitable way. In one example, neuromodulation stimulator device 302 is directly connected to at least one electrode 308. In another example, where at least one electrode 308 is implanted, neuromodulation stimulator device 302 is connected to at least one electrode 308 via a wireless connection.

Referring to FIG. 3, in this example, neuromodulation stimulator device 302 includes first signal generator 304, second signal generator 306 and database system 310. First signal generator 304, second signal generator 306 and database system 310 may include software and/or hardware components, such as a field programmable gate array (FPGA) or an application specific integrated circuit (ASIC), which performs certain tasks. First signal generator 304, second signal generator 306 and database system 310 may advantageously be configured to reside on an addressable storage medium and configured to be executed on one or more processors. Thus, first signal generator 304, second signal generator 306 and database system 310 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules.

Database system 310 may include a wide variety of data. For example, database system may include any of the following data: user data, application program data, content data, statistical data, historical data, databases, programs, files, libraries, pricing data and/or other data, etc.

In some example embodiments, at least one electrode 308 includes single or multiple arrays and may be placed on the skin overlying the spinal cord, spinal nerve(s), nerve root(s), ganglia, peripheral nerve(s), brain stem or target areas such as skeletal muscles.

In some embodiments, the at least one electrode is made of a conducting gel or reservoir of water soluble/salt solution. In some embodiments, the implantable electrodes are made of biocompatible material such as silicone and may be embedded with an inert metal such as gold or platinum wires.

Figure 4:
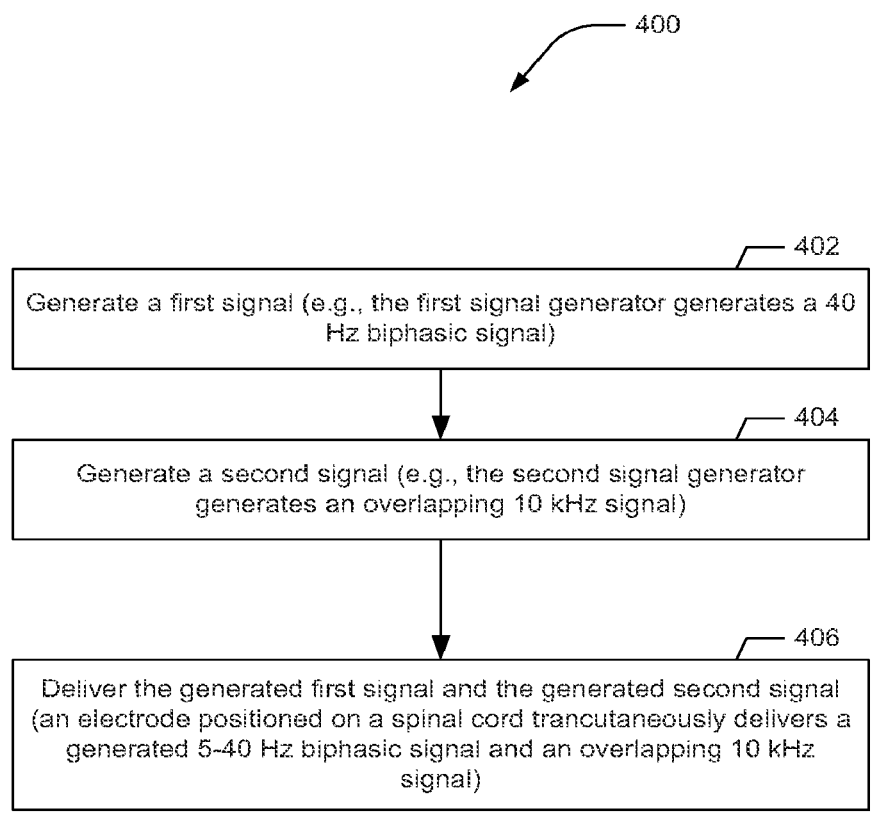
FIG. 4 is a flowchart illustrating an example procedure for delivering a generated first signal and a generated second signal.

As illustrated in FIG. 4, a flowchart of an example process 400 includes delivering a generated first signal and a generated second or overlapping signal. Process 400 may be embodied in one or more software programs which are stored in one or more memories and executed by one or more processors. Although process 400 is described with reference to the flowchart illustrated in FIG. 4, it should be appreciated that many other methods of performing the acts associated with process 400 may be used. For example, the order of many of the steps may be changed, some of the steps described may be optional, and additional steps may be included.

More specifically, in one example, the neuromodulation system generates a first signal, as indicated by block 402. For example, first signal generator 302 may generate a 40 Hz biphasic signal.

As indicated by block 404, the neuromodulation system generates a second signal. For example, second signal generator 304 may generate an overlapping 10 kHz signal.

As indicated by block 406, the neuromodulation system delivers the generated first signal and the generated second signal. For example, the neuromodulation system may transcutaneoulsy deliver, via an electrode positioned on a spinal cord, the generated 40 Hz biphasic signal with the overlapping 10 kHz signal.

Figure 5A:
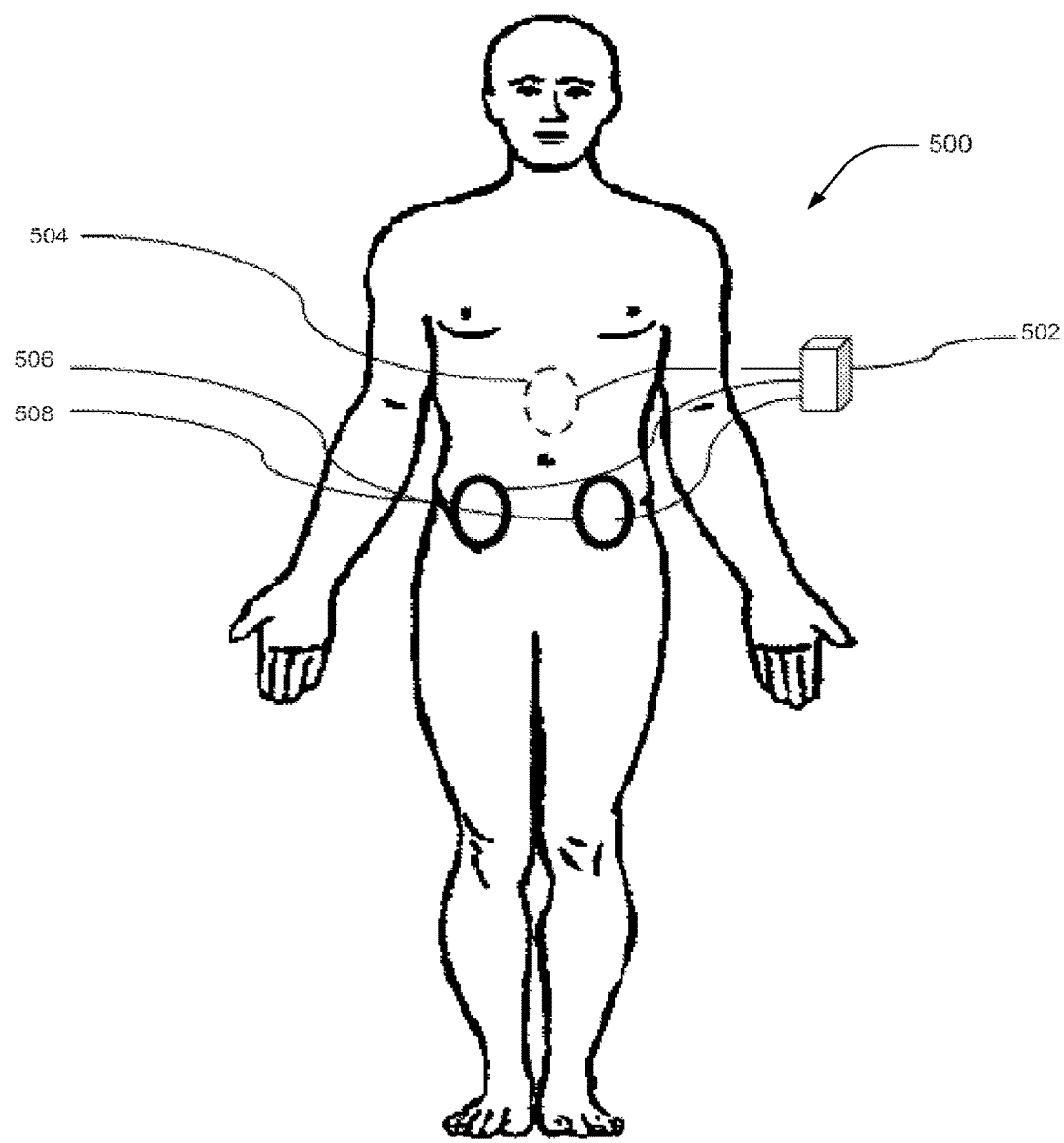
FIGS. 5A and 5B are diagrammatic views of an example neuromodulation system, illustrating an example arrangement or placement of a plurality of electrodes.
Figure 5B:
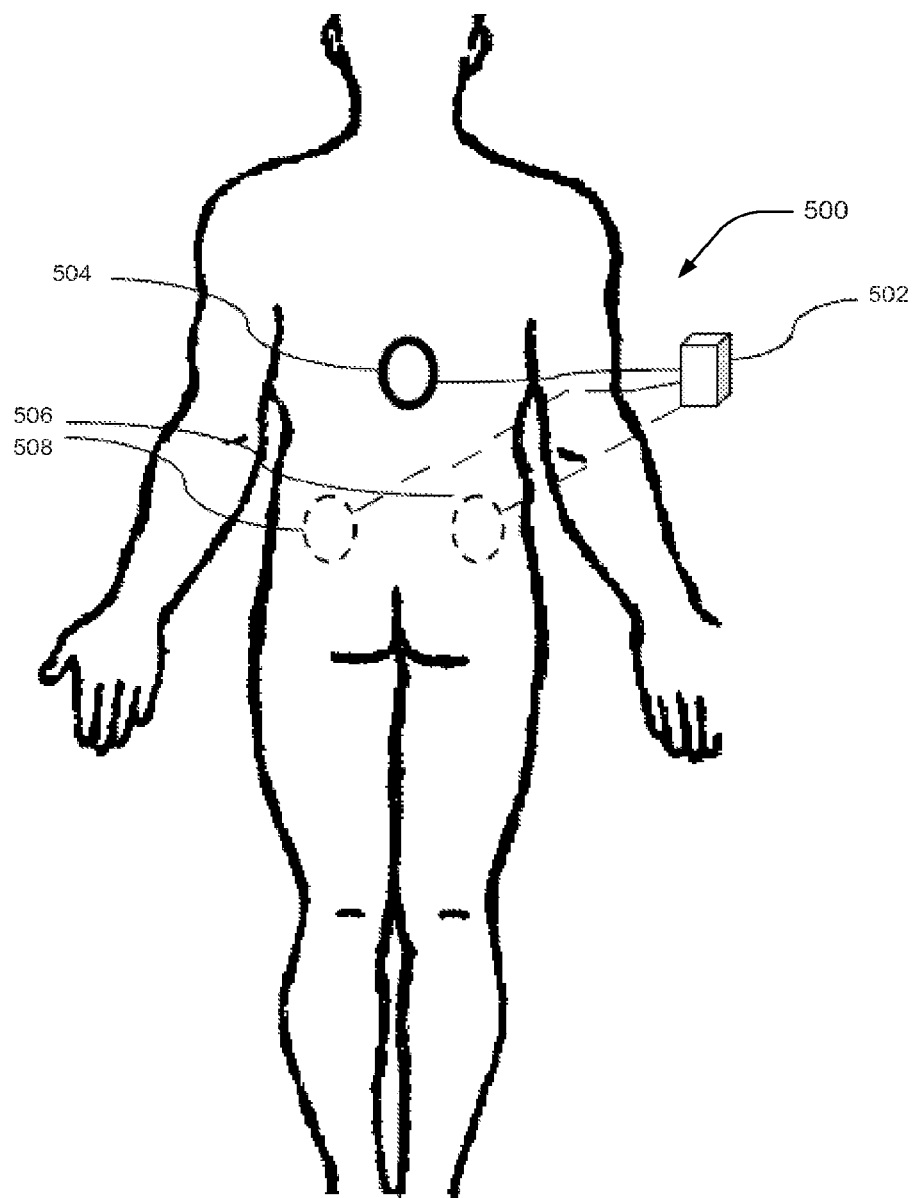

FIGS. 5A and 5B are diagrammatic views of an example neuromodulation system 500, illustrating an example arrangement or placement of a plurality of electrodes. In this example embodiment, neuromodulation system 500 includes trancutaneous electrical stimulator 502 which is operatively connected to at least one electrode or active electrode 504, first ground electrode 506 and second ground electrode 508. As best shown in FIG. 5B, in this example arrangement, active electrode 504 is disposed on the user's trunk. Such a configuration enables the neuromodulation system to deliver symmetrical activation.

Figure 6:
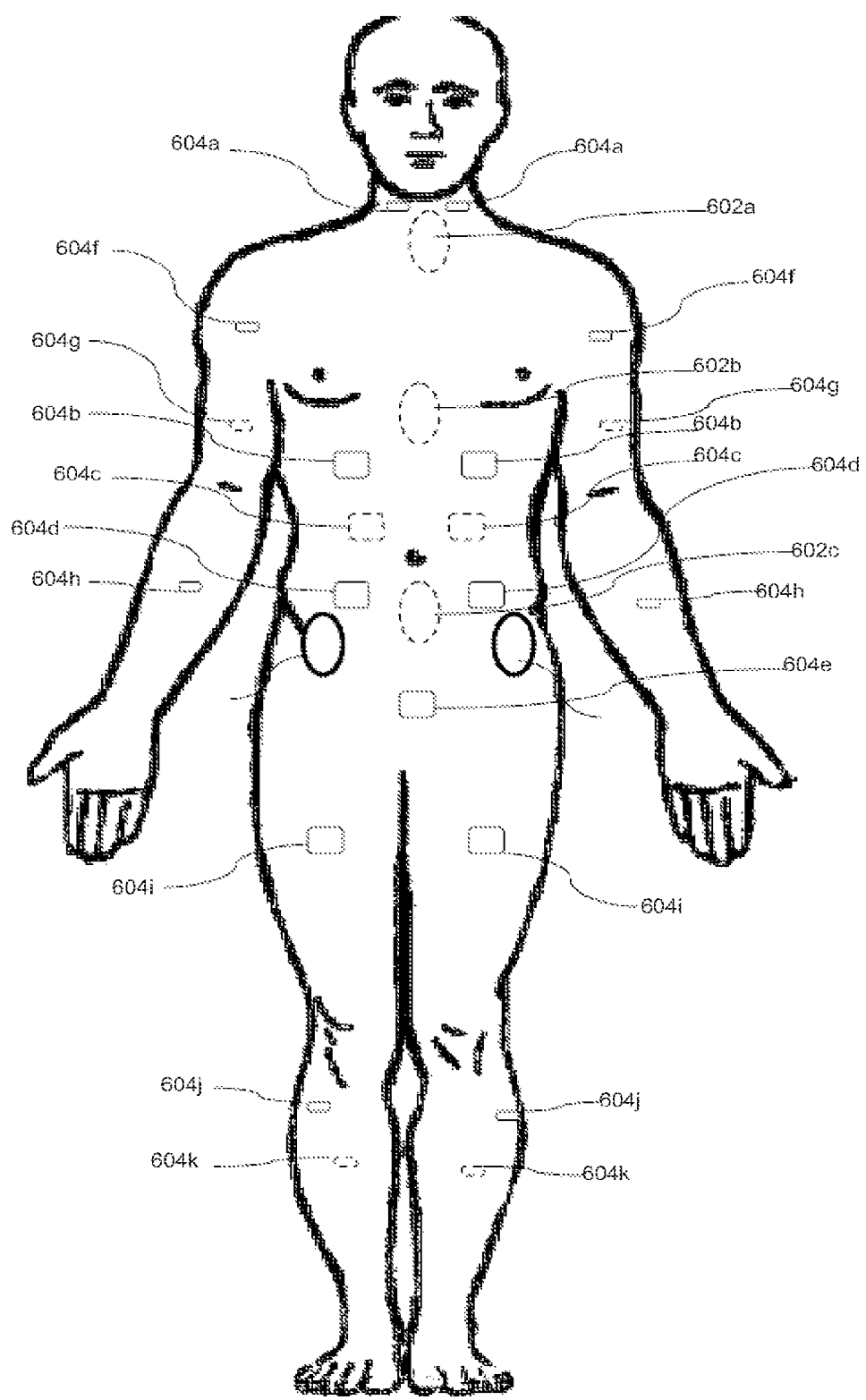
FIG. 6 is a diagrammatic view of alternative arrangements of different types of electrodes.

FIG. 6 is a diagrammatic view of alternative arrangements of different types of electrodes.

An active electrode may be placed in any suitable location. For example, as shown in FIG. 6, an active electrode may be placed overlying the user's neck, as shown by 602a, overlying the user's trunk, as shown by 602b, overlying the user's lower back, as shown by 602c, and/or overlying the base of a skull (i.e., the brainstem) (not shown).

As illustrated in FIG. 6, superficial electrodes may be positioned in a plurality of different locations. For example, superficial electrodes 604a are positioned overlying muscles of the neck or throat. Superficial electrodes 604b may be positioned overlying muscles of the diaphragm. Superficial electrodes 604c may be positioned overlying the kidney region. Superficial electrodes 604d may be positioned overlying the stomach region. Superficial electrode 604e may be positioned overlying the pubic region. Superficial electrodes 604f may be positioned overlying the shoulder or upper arm. Superficial electrodes 604g may be positioned overlying the biceps or upper arm. Superficial electrodes 604h may be positioned overlying the forearm. Superficial electrodes 604i may be positioned overlying the upper leg or thigh. Superficial electrodes 604j may be positioned overlying the lower leg or calf. Superficial electrodes 604k may be positioned overlying the lower leg or shin. Superficial electrodes 604l may be positioned overlying muscles of the neck or throat.

In one example embodiment, at least one electrode is configured to be implanted in a user. In this example, system 100 includes an electrical stimulator which wirelessly communicates with the at least one implanted electrode. In one example embodiment, the transcutaneous electrical stimulator causes the implanted electrode to deliver the generated first signal and the generated second signal. In some embodiments, the at least one implanted electrode is configured to record data and wirelessly transmit the recorded data to the electrical stimulator. In some embodiments, where the at least one electrode is implanted, the at least one electrode is configured to deliver the first generated signal and not the second generated signal. That is, in this example, the second generated signal is not needed.

In some embodiments, system 100 is configured to wirelessly communicate with adjunctive or ancillary equipment such as the footwear described in U.S. Pat. No. 7,726,206 which is hereby incorporated by reference in its entirety. The adjunctive or ancillary equipment may include at least one of a drug pump, drug delivery systems, physical therapy or skeletal support systems.

Figure 7:
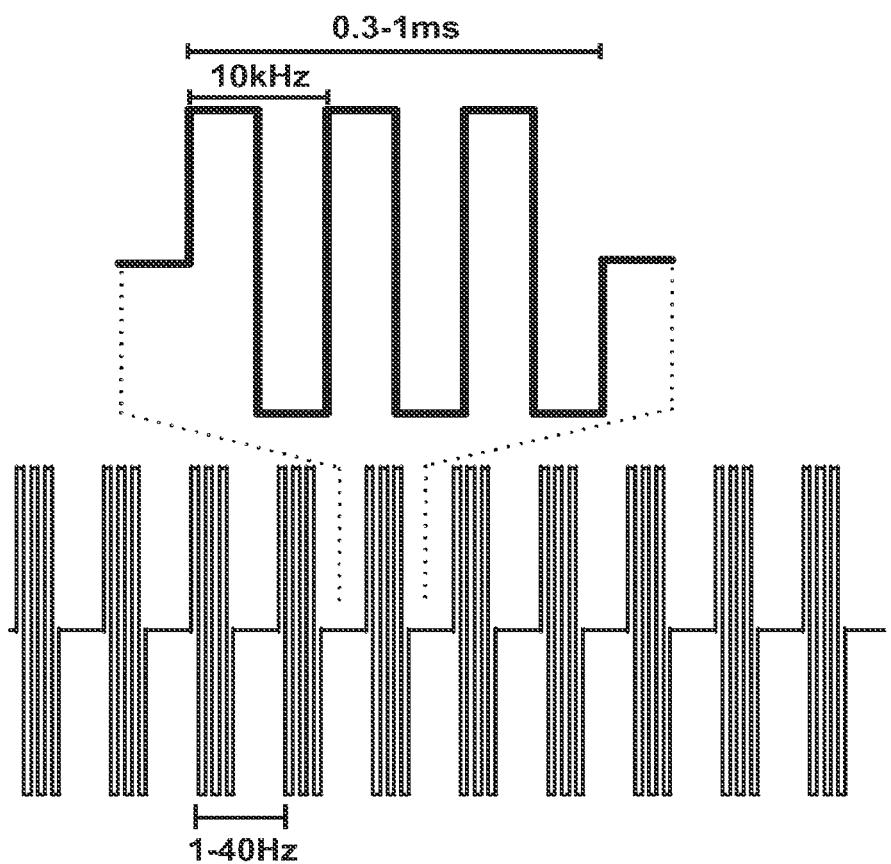
FIG. 7 is a diagrammatic view of an example signal which is delivered to a mammal.

As discussed above, in some embodiments, the neuromodulation system generates and delivers a first signal and a second signal. FIG. 7 illustrates one example of a signal which is delivered by the modulation system via at least one electrode. In this example, the signal is a 1-40 bipolar rectangular stimulus with a duration between 0.3 and 1.0 ms, filled with a carrier frequency of 5-10 kHz. The signal illustrated in FIG. 7 may result in less skin impedance, and more comfortable and relatively painless treatment which yields greater compliance and better outcomes.

In one example embodiment, the neuromodulation system includes a transistor (e.g., a push-pull transistor) which is configured to set the voltage of the delivered signal. The signal may be coupled through a transformer to patient channels or electrodes. Using switches, the channels or electrodes are activated and the signal is applied. The neuromodulation system may may include an opto-coupler current detection circuit. The signal may vary in duration, pulse frequency, pulse train duration and number of pulse trains.

In one example embodiment, for locomotion, the delivered signal is 30-40 Hz at 85-100 mA with an overlapping filling frequency of 10 kHZ.

The generated second or overlapping signal may have a frequency between 5 kHz and 10 kHz. In some embodiments, the generated second signal is adjustable between 5 kHz and 10 kHz.

In one example embodiment, the neuromodulation system is configured to deliver a bipolar rectangular stimulus with a pulse duration of 0.5 ms, filled with a carrier frequency of 10 kHz.

In one example embodiment, the neuromodulation system is configured to deliver biphasic stimuli filled with a carrier frequency of 10 kHz. In this example, the biphasic stimuli filled with a carrier frequency of 10 kHz may suppress the sensitivity of pain receptors of the subject. In another example embodiment, the neuromodulation system is configured to deliver biphasic stimuli filled with a carrier frequency of 5-10 kHz.

In some embodiments, the neuromodulation system sums the first generated signal and the second generated signal to generate a signal that is delivered to the electrode. In some embodiments, the neuromodulation system includes a frequency mixer configured to add or sum the first generated signal and the second generated signal.

In some embodiments, the neuromodulation system is configured to send different frequencies to two or more different electrodes which may be spatially separated on the surface of a patient's body.

In some embodiments, the neuromodulation system synchronizes the phasing between the first generated signal and the second generated signal at one point in time. In some embodiments, where the higher frequency is an integer multiple of the lower frequency, the neuromodulation system repeatedly synchronizes the phasing between the first generated signal and the second generated signal.

In one example embodiment, electrical stimulation is delivered at 1-100 Hz and at 30-200 mA.

In one example embodiment, electrical stimulation is delivered at 5-40 Hz and at one of 0-300 mA, 1-120 mA, 20-100 mA and 85-100 mA.

In one example embodiment, the frequency of the delivered signal is adjustable. In some embodiments, the frequency of the first generated signal is adjustable from 0.0-40 Hz.

In some embodiments, the pulse duration of the delivered signal is adjustable. In some embodiments, the pulse duration of at least one of the generated signals is adjustable from 0.5-3.0 ms.

In some embodiments, the amount of amplitude of the delivered signal is adjustable. In some embodiments, the amplitude is adjustable from 0-300 mA.

In some embodiments, the stimulation is continuous. In some embodiments, the stimulation is intermittent.

In some embodiments, the system enables ongoing identification of the optimal stimulation pattern, and allows for adjustment of the stimulating pattern by: (a) auto regulation; (b) direct manual control; or (c) indirect control though wireless technology.

In some embodiments, the neuromodulation system is configured to adjust stimulation and control parameters of the stimulator to levels that are safe and efficacious using parameters chosen to target specific neural components, or end organs and customized to each patient based on response to evaluation and testing.

In some embodiments, the system targets specific components of the nervous system with a desired predetermined stimulation parameter or series of stimulation parameters. In one example, in the case of locomotion, a monopolar electrode is placed over the paravertebral spaces of the thoracic vertebrae of T11-T12, with a reference electrode placed over the abdomen; the system is programmed to deliver 5-40 Hz signal at 85-100 mA with an overlapping high frequency pulse of 10 kHz.

In some embodiments, the neuromodulation system includes at least one sensor. In one example embodiment, the neuromodulation system determines stimulation parameters based on physiological data collected by the at least one sensor.

The at least one sensor may include at least one of an Electromyography ("EMG") sensor, a joint angle (or flex) sensor, an accelerometer, a gyroscope sensor, a flow sensor, a pressure sensor, a load sensor, a surface EMG electrode, a foot force plate sensor, an in-shoe sensor, an accelerator, a motion capture system, and a gyroscope sensor attached to or positioned adjacent the body of the subject.

The stimulation parameters may identify a waveform shape, amplitude, frequency, and relative phasing of one or more electrical pulses delivered to one or more pairs of the plurality of electrodes.

The at least one sensor may be connected to the neuromodulation system in any suitable way. For example, the at least one sensor may be connected via wires or wirelessly.

In some embodiments, the neuromodulation system includes at least one recording electrode. The neuromodulation system may be configured to receive and record electrical signals received from the at least one recording electrode. The at least one recording electrode may be positioned on an electrode array. The electrode array may be considered a first electrode array, and the system may include a second electrode array. The at least one recording electrode may be positioned on at least one of the first electrode array and the second electrode array. In some embodiments, the neuromodulation system includes a recording subsystem which is configured to record signals from the at least one recording electrode. The recording subsystem may include amplifiers which may be implemented as low noise amplifiers with programmable gain.

In some embodiments, the neuromodulation system includes a plurality of muscle electrodes which cause muscle to move (e.g., contract) to augment the improved neurological function provided by the complex stimulation patterns alone. The neuromodulation system may deliver electrical stimulation to the plurality of muscle electrodes.

In some embodiments, the neuromodulation system includes a stimulator device operatively connected to the electrodes. The stimulator device may include a casing which is configured to house a signal generator and a control module. The signal generator may be configured to signal generate the signals discussed herein. The control module may be configured to control the signal generator. The casing may be made of molded plastic and may be made compact and portable for single patient use.

The neuromodulation system may be configured to determine a set of stimulation parameters by performing a machine learning method based on signals received from a sensor. In one example, the machine learning method implements a Gaussian Process Optimization.

In one example embodiment, the neuromodulation system includes a plurality of electrodes. In this example, the neuromodulation system delivers stimulation or generated signals via a selected one or more of the electrodes.

In some embodiments, the neuromodulation system may be configured with at least one of the following properties or features: (a) a form factor enabling the neurostimulator device to be worn; (b) a power generator with rechargeable battery; (c) a secondary back up battery; (d) electronic and/or mechanical components encapsulated in a package made from one or more synthetic polymer materials; (d) programmable and autoregulatory; (e) ability to record field potentials; (f) ability to operate independently, or in a coordinated manner with other implanted or external devices; and (g) ability to send, store, and receive data via wireless technology.

In some embodiments, the system is capable of open and closed loop functionality, with the ability to generate and record field potentials, evoked potentials and/or modulate membrane potentials of cells and neuronal circuits.

In some embodiments, the stimulator device includes a rechargeable battery or AC current. In some embodiments, the stimulator device includes a dual power source (e.g., back up battery). In some embodiments, the system includes a power generator with a rechargeable battery.

In some embodiments, the non-invasive neurostimulator or neuromodulation devices may be used to deliver therapy to patients to treat a variety of symptoms or conditions such as post traumatic pain, chronic pain, neuropathy, neuralgia, epilepsy, spasm, and tremor associated with and without Parkinson's disease.

Unless defined otherwise, technical and scientific terms used herein have the same meaning as commonly understood by one of ordinary skill in the art to which this disclosure belongs.

The term "motor complete" when used with respect to a spinal cord injury indicates that there is no motor function below the lesion, (e.g., no movement can be voluntarily induced in muscles innervated by spinal segments below the spinal lesion.

The term "monopolar stimulation" refers to stimulation between a local electrode and a common distant return electrode.

The term "autonomic function" refers to functions controlled by the nervous system that are controlled largely below the level of consciousness, and typically involve visceral functions. Illustrative autonomic functions include, but are not limited to control of bowel, bladder, and body temperature.

The term "sexual function" refers to the ability to sustain a penile erection, have an orgasm (male or female), generate viable sperm, and/or undergo an observable physiological change associated with sexual arousal.

The term "cognitive function" refers to awareness of one's surrounding environment and the ability to function effectively, behaviorally, and mentally in a given environment.

It was discovered that transcutaneous electrical stimulation (tECS) of the spinal cord can induce activation locomotor circuitry in a mammal (e.g., in a human or a non-human mammal). It was demonstrated, for example, that continuous tESCS at 5-40 Hz applied paraspinally over T11-T12 vertebrae at 40-70 mA induced involuntary locomotor like stepping movements in subjects with their legs in a gravity-independent position. The increase of frequency of tSCS from 5 to 30 Hz resulted in augmentation of the amplitude of evoked stepping movements. In chronic spinal cats (3 weeks after spinal cord transection at Th8) tESCS at L5 (a frequency of 5 Hz and intensity ranged from 3 to 10 mA) evoked EMG stepping pattern in hindlimb muscles in all (N=4) of tested animals, while locomotor-like movements produced by tESCS were not weight-bearing.

By non-limiting example, transcutaneous electrical stimulation can be applied to facilitate restoration of locomotion and other neurologic function in subjects suffering with spinal cord injury, as well as other neurological injury and illness. Successful application can provide a device for widespread use in rehabilitation of neurologic injury and disease.

The neuromodulation system may facilitate movement in a mammalian subject (e.g., a human) having a spinal cord injury, brain injury, or other neurological disease or injury. In certain embodiments, the neuromodulation system is configured to stimulate the spinal cord of the subject using a surface electrode where the stimulation modulates the electrophysiological properties of selected spinal circuits in the subject so they can be activated by proprioceptive derived information and/or input from supraspinal. In some embodiments, stimulation may be accompanied by physical training (e.g., movement) of the region where the sensory-motor circuits of the spinal cord are located.

In some embodiments, the neuromodulation system is configured to stimulate the spinal cord with electrodes that modulate the proprioceptive and supraspinal information which controls the lower limbs during standing and/or stepping and/or the upper limbs during reaching and/or grasping conditions. It is the proprioceptive and cutaneous sensory information that guides the activation of the muscles in a coordinated manner and in a manner that accommodates the external conditions, e.g., the amount of loading, speed, and direction of stepping or whether the load is equally dispersed on the two lower limbs, indicating a standing event, alternating loading indicating stepping, or sensing postural adjustments signifying the intent to reach and grasp.

Unlike approaches that involve specific stimulation of motor neurons to directly induce a movement, the neuromodulation system described herein enables spinal circuitry to control the movements. More specifically, the neuromodulation system described herein exploits the spinal circuitry and its ability to interpret proprioceptive information and to respond to that proprioceptive information in a functional way. In some embodiments, this is in contrast to other approaches where the actual movement is induced/controlled by direct stimulation (e.g., of particular motor neurons).

In one example embodiment, a subject is fitted with one or more surface electrodes that afford selective stimulation and control capability to select sites, mode(s), and intensity of stimulation via electrodes placed superficially over, for example, the lumbosacral spinal cord and/or cervical spinal cord to facilitate movement of the arms and/or legs of individuals with a severely debilitating neuromotor disorder. The subject is provided the generator control unit and is fitted with an electrode(s) and then tested to identify the most effective subject specific stimulation paradigms for facilitation of movement (e.g., stepping and standing and/or arm and/or hand movement). Using these stimulation paradigms, the subject practices standing and stepping, reaching or grabbing, and/or breathing and speech therapy in an interactive rehabilitation program while being subject to spinal stimulation.

Depending on the site/type of injury and the locomotor activity it is desired to facilitate, particular spinal stimulation protocols include, but are not limited to, specific stimulation sites along the lumbosacral, thoracic, and/or cervical spinal cord; specific combinations of stimulation sites along the lumbosacral, thoracic, and/or cervical spinal cord and/or brainstem; specific stimulation amplitudes; specific stimulation polarities (e.g., monopolar and bipolar stimulation modalities); specific stimulation frequencies; and/or specific stimulation pulse widths.

In some embodiments, the neuromodulation system is designed so that the patient can use and control it in the home environment.

In some embodiments, the approach is not to electrically induce a walking pattern or standing pattern of activation, but to enable/facilitate it so that when the subject manipulates their body position, the spinal cord can receive proprioceptive information from the legs (or arms) that can be readily recognized by the spinal circuitry. Then, the spinal cord knows whether to step or to stand or to do nothing. In other words, this enables the subject to begin stepping or to stand or to reach and grasp when they choose after the stimulation pattern has been initiated.

Moreover, the neuromodulation system described herein is effective in a spinal cord injured subject that is clinically classified as motor complete; that is, there is no motor function below the lesion. In some embodiments, the specific combination of electrode(s) activated/stimulated and/or the desired stimulation of any one or more electrodes and/or the stimulation amplitude (strength) can be varied in real time, e.g., by the subject. Closed loop control can be embedded in the process by engaging the spinal circuitry as a source of feedback and feedforward processing of proprioceptive input and by voluntarily imposing fine tuning modulation in stimulation parameters based on visual, and/or kinetic, and/or kinematic input from selected body segments.

In some embodiments, the neuromodulation system is designed so that a subject with no voluntary movement capacity can execute effective standing and/or stepping and/or reaching and/or grasping. In addition, the approach described herein can play an important role in facilitating recovery of individuals with severe although not complete injuries.

In some embodiments, the neuromodulation system may provide some basic postural, locomotor and reaching and grasping patterns to a user. In some embodiments, the neuromodulation system may provide a building block for future recovery strategies. Based on certain successes in animals and some preliminary human studies (see below), it appears that a strategy combining effective transcutaneous stimulation of the appropriate spinal circuits with physical rehabilitation and pharmacological intervention can provide practical therapies for complete SCI human patients. Such an approach may be enough to enable weight bearing standing, stepping and/or reaching or grasping. Such capability can give SCI patients with complete paralysis or other neuromotor dysfunctions the ability to participate in exercise, which is known to be highly beneficial for their physical and mental health. In some embodiments, the neuromodulation system may enable movement with the aid of assistive walkers. While far from complete recovery of all movements, even simple standing and short duration walking would increase these patients' autonomy and quality of life. The neuromodulation system described herein (e.g., transcutaneous electrical stimulation) paves the way for a direct brain-to-spinal cord interface that could enable more lengthy and finer control of movements.

While the neuromodulation system described herein are discussed with reference to complete spinal injury, it will be recognized that they can apply to subjects with partial spinal injury, subjects with brain injuries (e.g., ischemia, traumatic brain injury, stroke, and the like), and/or subjects with neurodegenerative diseases (e.g., Parkinson's disease, Alzheimer's disease, Huntington's disease, amyotrophic lateral sclerosis (ALS), primary lateral sclerosis (PLS), cerebral palsy, and the like).

In some embodiments, the neuromodulation system may be used in conjunction with physical training (e.g., rigorously monitored (robotic) physical training) and optionally in combination with pharmacological techniques. The neuromodulation system enables the spinal cord circuitry to utilize sensory input as well as newly established functional connections from the brain to circuits below the spinal lesion as a source of control signals. The approach is thus designed to enable and facilitate the natural sensory input as well as supraspinal connections to the spinal cord in order to control movements, rather than induce the spinal cord to directly induce the movement. That is, the neuromodulation system facilitates and enhances the intrinsic neural control mechanisms of the spinal cord that exist post-SCI, rather than replace or ignore them.

Processing of Sensory Input by the Lumbosacral Spinal Cord: Using Afferents as a Source of Control In some embodiments, the neuromodulation exploits spinal control of locomotor activity. For example, the human spinal cord may receive sensory input associated with a movement such as stepping, and this sensory information can be used to modulate the motor output to accommodate the appropriate speed of stepping and level of load that is imposed on lower limbs. Moreover, the human lumbosacral spinal cord has central-pattern-generation-like properties. Thus, oscillations of the lower limbs can be induced simply by vibrating the vastus lateralis muscle of the lower limb, by transcutaneous stimulation, and by stretching the hip. The neuromodulation system exploits the fact that the human spinal cord, in complete or incomplete SCI subjects, can receive and interpret proprioceptive and somatosensory information that can be used to control the patterns of neuromuscular activity among the motor pools necessary to generate particular movements (e.g., standing, stepping, reaching, grasping, and the like). The neuromodulation system described herein facilitates and adapts the operation of the existing spinal circuitry that generates, for example, cyclic step-like movements via a combined approach of transcutaneous stimulation, physical training, and, optionally, pharmacology.

Facilitating Stepping and Standing in Humans Following a Clinically Complete Lesion Locomotion in mammals is attributed to intrinsic oscillating spinal neural networks capable of central pattern generation interacting with sensory information (Edgerton et al., *J. American Paraplegia Soc*, 14(4) (1991), 150-157; Forssberg, *J. Neurophysiol*, 42(4): 936-953 (1979); Grillner and Wallen, *Annu. Rev. Neurosci.*, 8: 233-261 (1985); Grillner and Zangger, *Exp Brain Res*, 34(2): 241-261 (1979)). These networks play critical roles in generating the timing of the complex postural and rhythmic motor patterns executed by motor neurons.

As indicated above, the neuromodulation system described herein can involve stimulation of one or more regions of the spinal cord in combination with locomotory activities. Spinal stimulation in combination with locomotor activity results in the modulation of the electrophysiological properties of spinal circuits in the subject so they are activated by Proprioceptive information derived from the region of the subject where locomotor activity is to be facilitated. Further, spinal stimulation in combination with pharmacological agents and locomotor activity results in the modulation of the electrophysiological properties of spinal circuits in the subject so they are activated by proprioceptive information derived from the region of the subject where locomotor activity is to be facilitated.

Locomotor activity of the region of interest can be accomplished by any of a number of methods known, for example, to physical therapists. By way of illustration, individuals after severe SCI can generate standing and stepping patterns when provided with body weight support on a treadmill and manual assistance. During both stand and step training of human subjects with SCI, the subjects can be placed on a treadmill in an upright position and suspended in a harness at the maximum load at which knee buckling and trunk collapse can be avoided. Trainers positioned, for example, behind the subject and at each leg assist as needed in maintaining proper limb kinematics and kinetics appropriate for each specific task. During bilateral standing, both legs can be loaded simultaneously and extension can be the predominant muscular activation pattern, although co-activation of flexors can also occur. Additionally, or alternatively, during stepping the legs are loaded in an alternating pattern and extensor and flexor activation patterns within each limb also alternated as the legs moved from stance through swing. Afferent input related to loading and stepping rate can influence these patterns, and training has been shown to improve these patterns and function in clinically complete SCI subjects.

Transcutaneous Stimulation of the Lumbosacral Spinal Cord

As indicated above, without being bound by a particular theory, it is believed that transcutaneous stimulation (e.g., over the throacic spinal cord) in combination with physical training can facilitate recovery of stepping and standing in human subjects following a complete SCI.

Spinal cord electrical stimulation has been successfully used in humans for suppression of pain and spasticity (see, e.g., Johnson and Burchiel, *Neurosurgery*, 55(1): 135-141 (2004); discussion 141-142; Shealy et al., *AnesthAnalg*, 46(4): 489-491 (1967); Campos et al., *Appl. Neurophysiol.* 50(1-6): 453-454 (1987); Dimitrijevic and Sherwood, *Neurology*, 30 (7 Pt 2): 19-27 (1980); Barolat *Arch. Med. Res.*, 31(3): 258-262 (2000); Barolat, *J. Am. Paraplegia Soc.*, 11(1): 9-13 (1988); Richardson et al., *Neurosurgery*, 5(3): 344-348). Recent efforts to optimize stimulation parameters have led to a number of research studies focusing on the benefits of transcutaneous spinal cord stimulation. The location of the electrode and its stimulation parameters are important in defining the motor response. Use of surface electrode(s), as described herein, facilitates selection or alteration of particular stimulation sites as well as the application of a wide variety of stimulation parameters.

The following non-limiting examples are offered for illustrative purposes.

Example 1: Transcutaneous Electrical Stimulation of the Spinal Cord: A Noninvasive Tool for the Activation of Stepping Pattern Generators in Humans A noninvasive method for activating the SN by means of transcutaneous electrical spinal cord stimulation (tESCS) is demonstrated in this Example. The method is based on our research that showed that a single dermal electric stimulus applied in the region of the T11-T12 vertebrae caused monosynaptic reflexes in the proximal and distal leg muscles in healthy subjects (see Courtine, G., Harkema S. J, Dy, C. J., Gerasimenko, Yu. P., and Dyhre-Poulsen, P., Modulation of Multisegmental Monosynaptic Responses in a Variety of Leg Muscles during Walking and Running in Humans, J Physiology, 2007, vol. 585, p. 1125) and in patients with clinically complete (ASIA A) spinal cord injury. See Dy, C. J., Gerasimenko, Y P., Edgerton, V R., DyhrePoulsen P., Courtine G., Harkema S., Phase-Dependent Modulation of Percutaneously Elicited Multisegmental Muscle Responses after Spinal Cord Injury, *J Neurophysiol.*, 2010, vol. 103, p. 2808. Taking into consideration that eESCS affects the SN through mono and polysynaptic reflexes (see Minassian, Persy, Rattay, Pinter, Kern, and Dimitrijevic, supra), we suggest that noninvasive tESCS can be an effective way to neuromodulate the SN.

Experiment

We examined six healthy adult male subjects (students and staff of the Velikie Luki State Academy of Physical Education and Sports). They had given their informed written consent to participate in the experiment. The experiment was approved by the Ethics Committee of the academy and met the requirements of the Helsinki Declaration.

The subjects lay on a couch on their left side, with their feet placed on separate boards that were attached to a hook in the ceiling of the experimental room with ropes, like swings. The right (upper) leg was supported directly in the region of the shank. The left (lower) leg was placed in a rotating frame attached to a horizontal board. Under these conditions, the subjects could move their legs through maximum amplitude: According to the instructions, the subjects lay quietly and neither counteracted nor facilitated the movements caused by electrical stimulation of the spinal cord.

The tESCS was performed using a KULON stimulator (St. Petersburg State University of Aerospace Instrumentation, St. Petersburg, Russia). The stimulation was administered using a 2.5 cm round electrode (Lead-Lok, Sandpoint, United States) placed midline on the skin between the spinous processes of T11 and T12 as a cathode and two 5.0×10.2 cm rectangular plates made of conductive plastic (Ambu, Ballerup, Germany) placed symmetrically on the skin over the iliac crests as anodes. The step-like movements were evoked by a bipolar rectangular stimulus with a duration of 0.5 ms, filled with a carrier frequency of 10 kHz; the intensity of stimulation ranged from 30 to 100 mA. The stimulation frequencies were 1, 5, 10, 20, 30, and 40 Hz; the duration of exposure ranged from 10 to 30 s. During the high-frequency stimulation within each stimulus, tESCS did not cause pain even when the amplitude was increased to 100 mA or more; allowing us to study in detail the dependence of the elicited movements on the amplitude and frequency of the stimulus.

The EMGs of the muscles of both legs (m. rectus femoris, m. biceps femoris, m. tibialis anterior, and m. gastrocnemius) were recorded by means of bipolar surface electrodes. EMG signals were recorded using an ME 6000 16-channel telemetric electroneuromyograph (Mega Win, Finland). Flexion-extension movements in the knee joints were recorded using a goniometer.

The Qualisy video system (Sweden) was used to record the kinematic parameters of leg movements. Light-reflecting markers were attached to the pivot points of the body, which coincided with the rotational axis in the shoulder, hip, knee, and ankle joints. The angular movements in the hip joint were calculated from the location of markers on the lateral epicondyle of the humerus, trochanter, and lateral epicondyle of the femur. The markers that were attached to the trochanter, lateral epicondyle of the femur, and lateral ankle were used to describe the movements in the knee joint. The movements in the ankle joint were estimated by means of the markers located on the lateral epicondyle of the femur, lateral ankle, and the big toe. The reconstruction of movements in one whole step cycle was performed by means of a special software. In order to record the movements of the foot tip, the marker was fixed on the big toe of the right foot.

The recording of EMG was synchronized with the recording of stepping kinematical parameters. The average cycle duration and the amplitudes of angular movements were calculated from 10-12 cycles. The duration of a step cycle was calculated on the basis of the interval between two maximum values of angular movements in the hip, knee, and ankle joints. The phase shift between the hip and knee joints was calculated from the interval between the maximum values of angular movements in these joints.

The statistical treatment of the data was performed using a standard software package.

Results

Transcutaneous electrical spinal cord stimulation with a frequency of 5-40 Hz elicited involuntary leg movements in five out of six subjects. The threshold intensity of the stimulus that induced involuntary movements was 50-60 mA and was dependent on the frequency of stimulation. The tESCS at a frequency of 1 Hz caused reflex responses in the leg muscles with a threshold of 70-80 mA (FIG. 8a).

Figure 8:
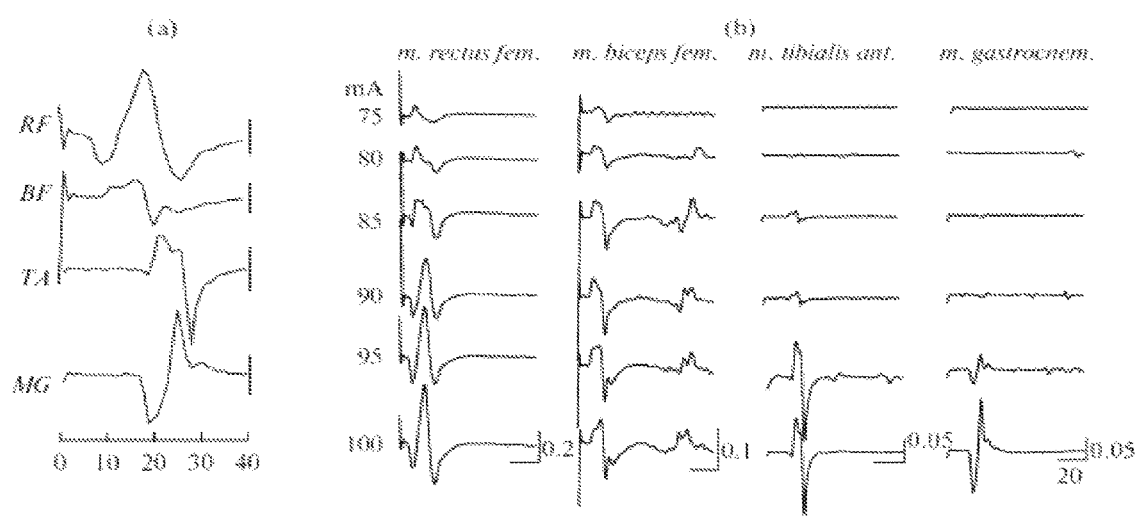
FIG. 8, panels a and b, show motor responses in the muscles of the right leg to the tESCS with a frequency of 1 Hz and an amplitude of 75-100 mA (showed at the left of the recordings). The responses in the m. rectus femoris and m. biceps femoris (RF and BF, respectively), as well as in the m. tibialis anterior and m. gastrocnemius (TA and MG, respectively) are shown. At the right bottom of the lower recording, there are marks of time in ms, the same for all the muscles, and marks of the amplitude in mV.

Original records of EMG responses in the muscles of the right leg to the tESCS at a frequency of 1 Hz and intensity of 75-100 mA are shown in FIG. 8. Increasing stimulus intensity resulted in an increase in the amplitude of responses. First, the hip muscles (m. rectus femoris and m. biceps femoris) were involved in the motor response; then, the shank muscles (m. tibialis anterior and m. gastrocnemius) were involved (FIG. 8b). The response to each stimulus is composed of the early monosynaptic responses (the same is shown in Courtine, Harkema, Dy, Gerasimenko, and Dyhre-Poulsen, supra) with a latency period of about 12-15 ms. Increasing stimulus intensity evoked responses in the biceps femoris muscle (flexor) with a latent period of a few tens of milliseconds, which were, apparently, polysynaptic. Thus, tESCS with a low frequency (1 Hz) elicited reflex responses in the leg muscles that contained mono and polysynaptic components.

Figure 9A:
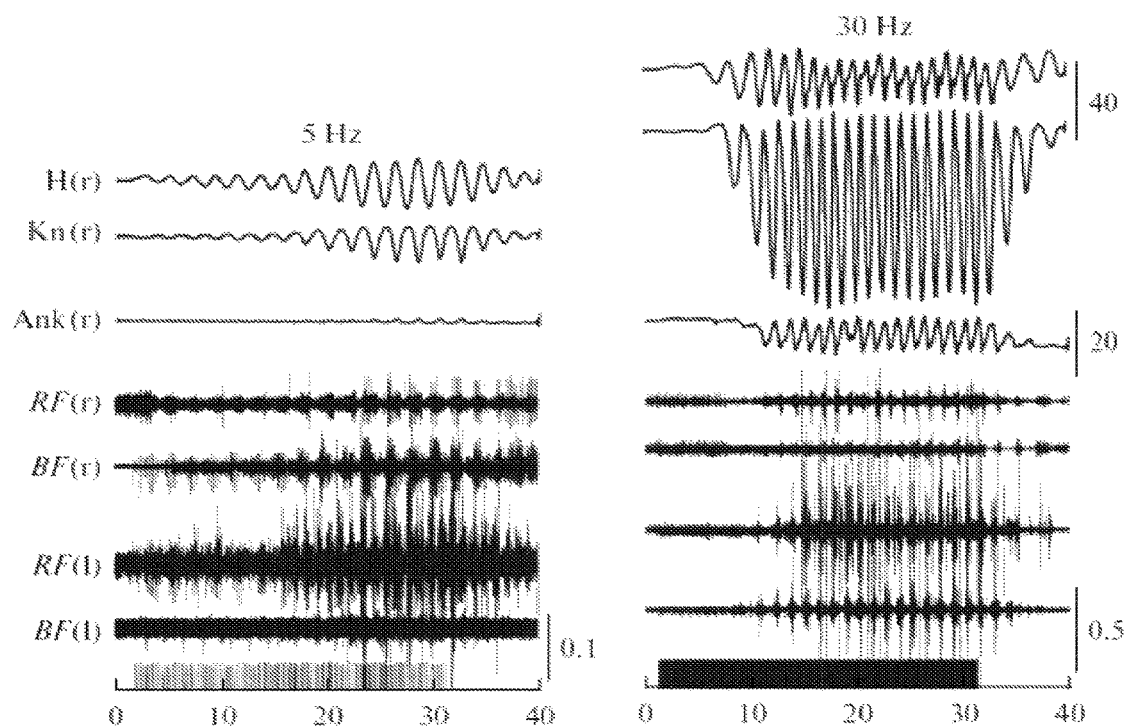
FIGS. 9A and 9B show electrical activity of the leg muscles and movements in the leg joints evoked by tESCS with frequencies of 5 and 30 Hz.
Figure 9B:
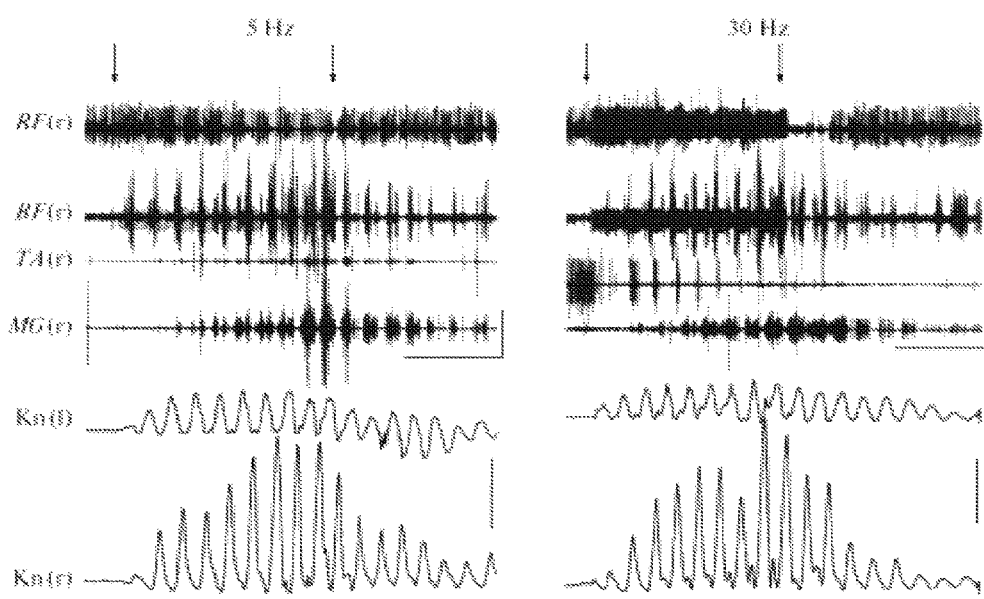

Transcutaneous electrical spinal cord stimulation at frequencies in the entire range from 5 to 40 Hz caused step-like movements in five subjects (FIG. 9). There was some variability in the ability of tESCS to evoke step-like movements at different frequencies of stimulation. In two subjects (R. and S.), step-like movements were evoked by tESCS at all the test frequencies in the range 5-40 Hz; in subjects K and G., they were recorded at frequencies of 5, 10, 20, and 30 Hz; and in subject B, they were recorded at frequencies of 5 and 30 Hz. The latent period of the starting of movements did not depend on the frequency of stimulation and was in the range of 0.2-2.5 s. The amplitude of movements in subjects S, G, and R at the beginning of stimulation gradually increased to the maximum, and after its termination it gradually decreased. In subjects K and V, the movements terminated against the background of ongoing tESCS, the duration of the stepping pattern was approximately 10-20 s. In subjects R and S, the movements continued during the whole period of stimulation and ended 2-4 s after its termination.

Pair wise comparison of the mean amplitudes of the movements of the hip, knee, and ankle joints calculated during the first and the last 15 s of stimulation at each of the frequencies used allowed us to determine the probability of the differences in the amplitudes of the induced movements at the beginning and at the end of the stimulation (see Table 1, below). Two rows of probabilities for subject C, calculated on the bases of two experiments show the different direction of the changes in the amplitudes at the beginning and end of stimulation. In the table, the cases when the amplitude of movements at the end of the stimulation was significantly greater than in the beginning are boldfaced; the cases when the amplitude of movements at the end of the stimulation was significantly lower than in the beginning are italicized. According to the data, the subjects were divided into two groups. In the first group (subjects R and S), step-like movements were evoked by the stimulation at the entire range of the frequencies studied (5-40 Hz), and the amplitude of movements, while growing at the beginning of stimulation, decayed after its termination. In the second group (subjects K and V), the movements were evoked with difficulty and with a limited set of frequencies. These differences could be related both to the individual characteristics of the electrical conductivity of the skin and to characteristics of the spinal connections.

Figure 10:
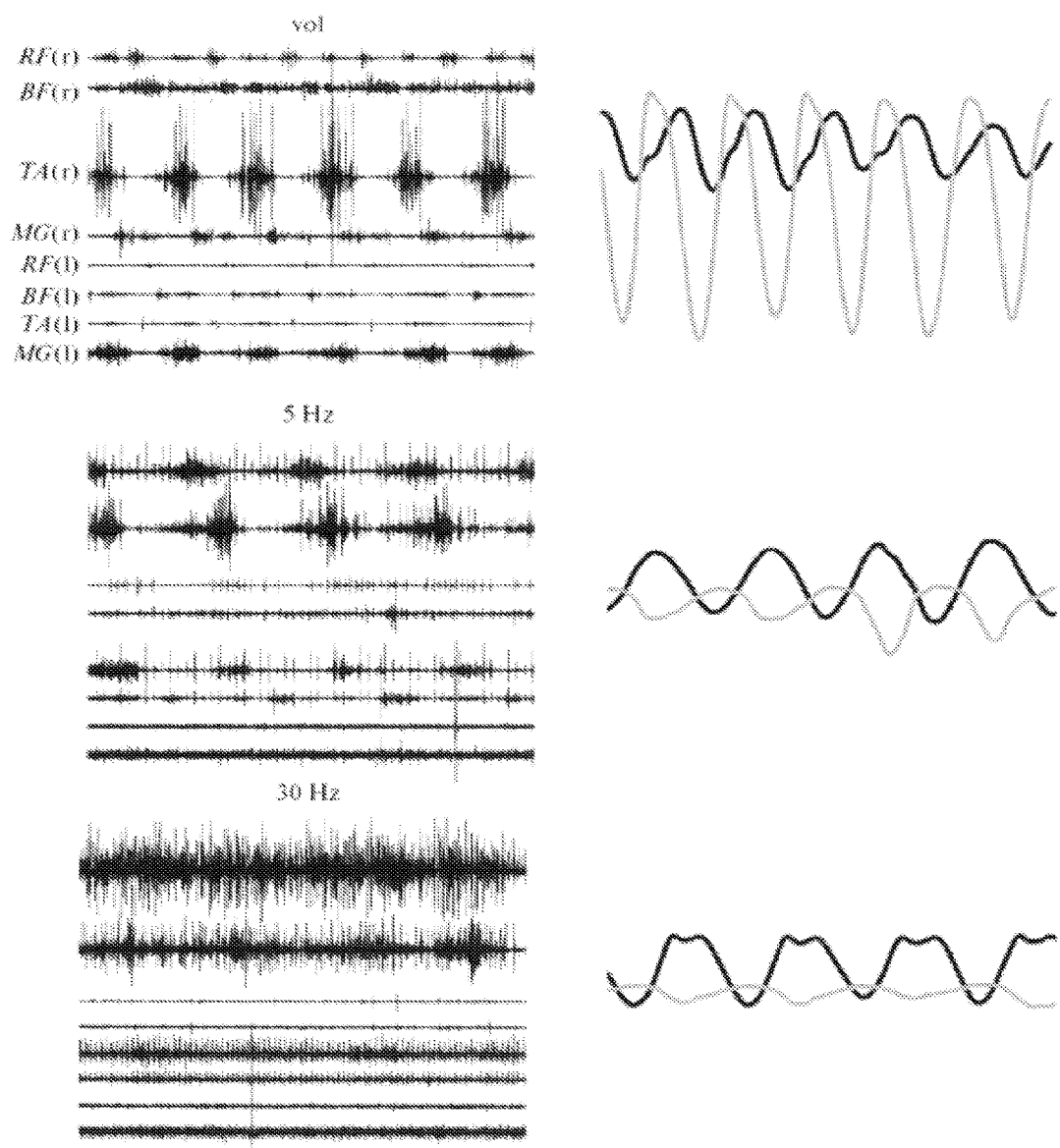
FIG. 10 EMGs (left) and trajectories of reflective markers attached to the right leg; kinematograms (right) recorded during voluntary stepping movements (vol) and movements caused by tESCS with frequencies of 5 and 30 Hz. The duration of records is 10 s. Black and gray lines show movements in the hip and knee joints, along with calibrations for changes in joint angles respectively. The remaining designations are the same as in FIG. 2.

The involuntary movements of the legs caused by tESCS fully complied with the characteristics of stepping movements (FIG. 10). Like voluntary stepping movements, the involuntary movements caused by tESCS surely contain the alternating contractions of the similar muscles of the left and right legs and the alternation of antagonist muscle activity in the hip and shin (rectus femoris and biceps femoris, gastrocnemius and tibial muscle of the shin). As clearly seen in the curves reflecting the motion of the hip and knee joints, the movements in these joints, both voluntary and evoked by tESCS, occurred with a phase shift (the motion in the knee ahead of the motion in the hip).

The table below shows the probability of similarity of the mean amplitudes of movements, measured in the first and the last 15 s during tESCS. For subject S., two different cases of stimulation are shown.

TABLE 1

| | | The Frequency of Stimulation | | | | |
|---|---|---|---|---|---|---|
| Subject | Joint | 5 Hz | 10 Hz | 20 Hz | 30 Hz | 40 Hz |
| S. (1) | H | 0.08 | 0.16 | 0.20 | 0.005 | 0.1 |
| | Kn | 0.003 | 0.26 | 0.41 | 0.03 | 0.0003 |
| | Ank | 0.08 | 0.07 | 0.18 | 0.20 | 0.07 |
| S. (2) | H | 0.01 | 0.0001 | 0.004 | 0.82 | 0.92 |
| | Kn | 0.04 | 0.0001 | 0.002 | 0.0004 | 0.12 |
| | Ank | 0.002 | 0.0006 | 0.002 | 0.001 | 0.08 |
| R. | H | 0.07 | 0.05 | 0.14 | 0.27 | *0.007* |
| | Kn | 0.0001 | 0.001 | 0.03 | 0.01 | 0.15 |
| | Ank | 0.02 | 0.008 | 0.003 | 0.47 | 0.68 |
| K. | H | 0.99 | | | *0.002* | |
| | Kn | *0.03* | | | *0.008* | |
| | Ank | 0.21 | | | *0.001* | |
| B. | H | *0.03* | 0.16 | 0.27 | 0.68 | |
| | Kn | 0.12 | 0.06 | *0.04* | *0.02* | |
| | Ank | *0.05* | 0.99 | 0.15 | *0.001* | |
| G. | H | *0.004* | 0.16 | 0.21 | 0.16 | |
| | Kn | *0.05* | 0.08 | 0.24 | 0.26 | |
| | Ank | *0.005* | *0.05* | 0.29 | *0.009* | |

Note:
H, hip joint;
Kn, knee joint;
Ank, ankle joint.
The cases where p ≤ 0.05 are boldfaced and italicized. Other explanations are in the text.

Figure 11:
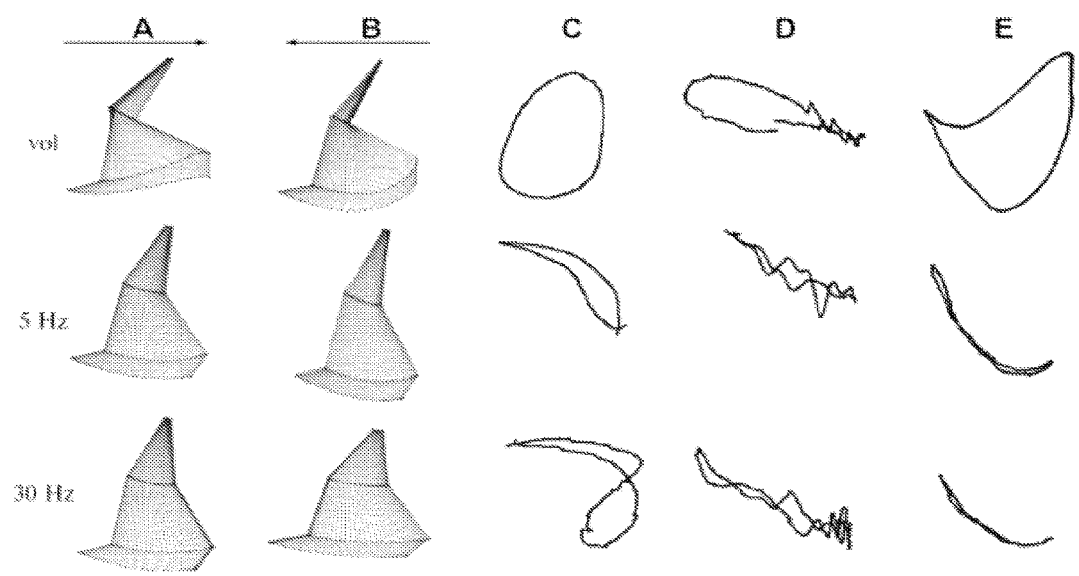
FIG. 11, panels A-E, show interarticular coordination during voluntary stepping movements (vol) and movements caused by tESCS with frequencies of 5 and 30 Hz. Reconstruction of the movements of the right leg during one stepping cycle obtained by processing the cinematograms of the (Panel A) forward and (Panel B) backward movements of legs, respectively; the coordination of movements in the (Panel C) hip and knee joints, (Panel D) knee and ankle joints; and (Panel E) the trajectory of a big toe. Subject R.

Stepping cycles in three joints of the right leg during voluntary stepping movements (FIG. 11a) and movements elicited by tESCS reconstructed based on the kinematic analysis and the trajectory of the tip of the foot (the big toe) are shown in FIG. 11. In step-like movements elicited by tESCS, as in voluntary stepping movements, the phase of carrying the leg forward and the phase of support during the backward leg movements were distinct (FIGS. 11a, 11b). During voluntary movements, the patterns of the knee and ankle joints are more complex than during the elicited movements. The coordination between the joints during the evoked movements is very different from that observed during voluntary movements (FIGS. 11c, 4d). The same is true for the movements of the distal region of the leg, resulting from the interaction of movements in all three joints, and recorded using a marker attached to the big toe (FIG. 11f). The trajectory of the terminal point in voluntary movements looked like an ellipse (FIG. 11f). The trajectory of the terminal point in the movements elicited by tESCS may be considered a confluent ellipse, with the leg moving forward and backward without significant vertical movements.

The frequency of step-like movements did not depend on the frequency of stimulation. The average periods of step-like movements in subjects R, S, K, B, and G were 2.72±0.14, 2.39±0.55, 2.42±0.15, 3.22±0.85, and 1.9±0.09 s, respectively.

Figure 12:
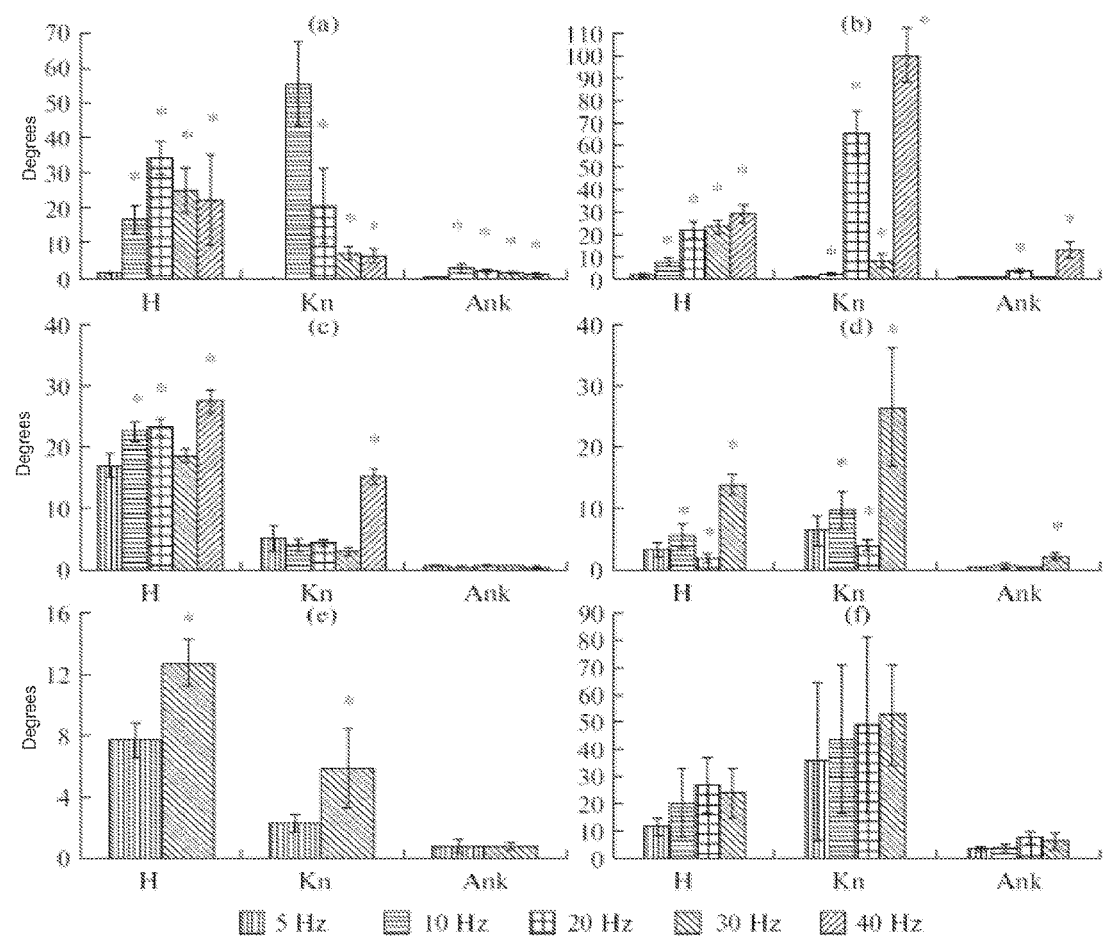
FIG. 12, panels a-e, show the average amplitude of movements in the hip (H), knee (Kn), and ankle (Ank) joints caused by tESCS with a frequency of 5-40 Hz recorded during the first 15 s after the start of stimulation. The ordinate shows angular degrees. (Panels a, b) Subject S, different strategies; (Panel b) subject R; (Panel c) subject B; (Panel d) subject E; (Panel e) subject G. Error bars, standard deviation. Asterisks, significant differences in amplitude recorded during tESCS with a frequency of 5 Hz, $p \leq 0.05$.

As mentioned above, the pair wise comparison of the mean amplitudes of the movements in the hip, knee, and ankle joints calculated in the first and the last 15 s of stimulation in different subjects, showed that, regardless of the stimulation frequency, the amplitude of movements may either increase or decrease significantly. At the beginning of stimulation, there was a tendency for the amplitude of movements to increase with increasing frequency of stimulation in all subjects for all joints (FIG. 12). However, at the end of stimulation, the amplitude of movements was independent of the stimulation frequency. In all joints, minimum movements were observed at a stimulation frequency of 5 Hz (FIGS. 12b, 12d). As an exception, only in one case, when subject S. was stimulated, the amplitude of movements in the hip joint increased with increasing stimulation frequency and the amplitude of movements in the knee and ankle joints decreased with increasing frequency [FIG. 12; table 1, subject S. (1)]. The trajectory of movement of the big toe of this subject, reflecting the amplitude of the whole leg's movement, is shown in FIG. 12a. In this case, the amplitude of movement of the tip of the foot at stimulation frequencies of 10, 20, 30, and 40 Hz was, respectively, 15.0, 19.9, 15.3, and 16.4 times greater than at 5 Hz. In the case shown in FIG. 12b, it was, respectively, 3.5, 9.4, 11.3, and 80.7 times greater than at 5 Hz. Thus, in this subject, with increasing frequency of stimulation, the amplitude of leg movements did not decrease in any of the cases; it was minimal at a frequency of 5 Hz.

Note that, in the cases shown in FIGS. 12b and 12d, an increase in frequency resulted in a significant increase in the amplitude of movements in the ankle joint. The possibility to control the movements in the ankle joint via the frequency of stimulation was an advantage of tECS, unlike the ankle joint which was not modulated in vibration-induced step-like movements. See Gorodnichev, Machueva, Pivovarova, Semenov, Ivanov, Savokhin, Edgerton, and Gerasimenko, supra.

Discussion

Transcutaneous electrical stimulation of the lumbar enlargement may strengthen the patterns of EMG activity in leg muscles in patients with complete or partial spinal cord lesions during assisted walking movements on a moving treadmill. See Minassian, Persy, Rattay, Pinter, Kern, and Dimitrijevic, supra. However, voluntary step-like movements were never successfully evoked by means of transcutaneous stimulation in this category of patients before. It was observed that transcutaneous electrical stimulation applied to the rostral segments of the lumbar enlargement (in the region of the T11-T12 vertebrae) elicited involuntary step-like movements in healthy subjects with their legs suspended in a gravity-neutral position. This phenomenon was observed in five out of the six subjects studied. tESCS did not cause discomfort and was easily tolerated by subjects when biphasic stimuli filled with a carrier frequency of 10 kHz which suppressed the sensitivity of pain receptors were used.

The Proof of the Reflex Nature of the Responses Evoked by tESCS

A single transcutaneous electrical stimulation in the region of the T11-T12 vertebrae causes responses in leg muscles with a latency period corresponding to monosynaptic reflexes. See Courtine, Harkema, Dy, Gerasimenko, and Dyhre-Poulsen, supra. It is assumed that these responses are due to the activation of large-diameter dorsal root afferents. See Minassian, Persy, Rattay, Pinter, Kern, and Dimitrijevic, supra; Dy, C. J., Gerasimenko, Y P., Edgerton, V R., DyhrePoulsen P., Courtine G., Harkema S., Phase-Dependent Modulation of Percutaneously Elicited Multisegmental Muscle Responses after Spinal Cord Injury, J Neurophysiol., 2010, vol. 103, p. 2808; de Noordhout, A., Rothwell, J. e., Thompson, P. D., Day, B. L., and Marsden, e. D., Percutaneous Electrical Stimulation of Lumbosacral Roots in Man, J Neurol. Neurosurg. Psychiatry, 1988, vol. 51, p. 174; Troni, W., Bianco, e., Moja, M. C., and Dotta, M., Improved Methodology for Lumbosacral Nerve Root Stimulation, Afuscle Nerve, 1996, vol. 19, no. Iss. 5, p. 595; Dyhre-Poulsen, P., Dy, e.1., Courtine, G., Harkema, S., and Gerasimenko, YU. P., Modulation of Multi segmental Monosynaptic Reflexes Recorded from Leg Muscles During Walking and Running in Human Subjects, Gait Posture, 2005, vol. 21, p. 66. The monosynaptic nature of these responses is confirmed by the fact that vibration of muscle tendons or paired stimulation suppresses the responses. We have previously shown that the responses to the second stimulus were suppressed in rats during epidural stimulation (see Gerasimenko, Lavrov, Courtine, Ronaldo, Ichiyama, Dy, Zhong, Roy, and Edgerton, supra) and in healthy humans (see Courtine, Harkema, Dy, Gerasimenko, and Dyhre-Poulsen, supra; Dy, Gerasimenko, Edgerton, Dyhre-Poulsen, Courtine, Harkema, supra) during paired tESCS with a delay between the stimuli of 50 ms. This refractory period excludes the possibility of direct activation of the motor neurons in the ventral horn or ventral root activation. See Struijk, 1.1., Holsheimer, 1., and Boom, H. B. K., Excitation of Dorsal Root Fibers in Spinal Cord Stimulation: A Theoretical Study, IEEE Trans. Biorned. Eng., 1993, vol. 40, no. 7, p. 632. The monosynaptic nature of the responses was also shown during vibration tests. It is well known that vibration suppresses monosynaptic reflex pathways in homologous muscles. See Mao, e. e., Ashby, P., Wang, M., and McCrea, D., Synaptic Connections from Large Muscle Afferents to the Motoneurons of Various Leg Muscles in Man, Exp. Brain Res., 1984, vol. 56, p. 341. The suppression of responses caused by tESCS in shin muscles during the vibration of the Achilles tendon directly shows the monosynaptic nature of these responses. The similarity of modulations of the classical monosynaptic H-reflex and reflex responses caused by tESCS during walking in healthy subjects (see Courtine, Harkema, Dy, Gerasimenko, and Dyhre-Poulsen, supra) and in patients with spinal cord injuries (see Dy, Gerasimenko, Edgerton, Dyhre-Poulsen, Courtine, Harkema, supra) also supports the monosynaptic nature of the responses to transcutaneous stimulation. In both cases, the amplitude of modulation of the reflexes was proportional and phase-dependent on the activation level of each muscle. All of the above data indicate the identity of the H-reflex and reflex responses induced by tESCS.

In the flexor muscles affected by tESCS, polysynaptic reflexes were sometimes recorded in addition to the monosynaptic component (FIG. 8). Earlier, we recorded polysynaptic reflexes in the flexor the intact and spinal animals during the single epidural stimulation. See Gerasimenko, Lavrov, Courtine, Ronaldo, Ichiyama, Dy, Zhong, Roy, and Edgerton, supra; Lavrov, 1., Gerasimenko, YU. P., Ichiyama, R., Courtine G., Zhong H., Roy R., and Edgerton R. V, Plasticity of Spinal Cord Reflexes after a Complete Transection in Adult Rats: Relationship to Stepping Ability, J Neurophysiol., 2006, vol. 96, no. 4, p. 1699. All the above data suggest that tESCS can activate mono and polysynaptic neuronal networks.

The Characteristics of Transcutaneous Stimulation Eliciting Step-Like Movements

The previous experiments showed that the rostral segments of the lumbar spinal cord may play the role of triggers in initiating locomotor movements. See Deliagina, T. G., Orlovsky, G. N., and Pavlova, G. A., The Capacity for Generation of Rhythmic Oscillations Is Distributed in the Lumbosacral Spinal Cord of the Cat, Exp. Brain Res., 1983, vol. 53, p. 81. In spinal patients (see Dimitrijevic, M. R, Gerasimenko, Yu., and Pinter, M. M., Evidence for a Spinal Central Pattern Generator in Humans, Ann. N. Y. Acad. Sci., 1998, vol. 860, p. 360) and in spinal rats (Ichiyama, R. M., Gerasimenko, YU. P., Zhong, H., Roy, R. R., and Edgerton V R., Hindlimb Stepping Movements in Complete Spinal Rats Induced by Epidural Spinal Cord Stimulation, New•osci. Lett., 2005, vol. 383, p. 339), step-like patterns of EMG activity were evoked by epidural stimulation of the L2 segment. In our experiments, we used transcutaneous electrical stimulation in the region of T11-T12 vertebrae, which corresponds to the cutaneous projection of the L2-L3 segments of the spinal cord. It was previously shown that the electromagnetic stimulation of this region in healthy subjects with their legs supported externally can initiate walking movements. See Gerasimenko, Gorodnichev, Machueva, Pivovarova, Semenov, Savochin, Roy, and Edgerton, supra; Gorodnichev, Machueva, Pivovarova, Semenov, Ivanov, Savokhin, Edgerton, and Gerasimenko, supra. These data are consistent with the current concept on the structural and functional organization of the SN with distributed pacemaking and pattern-generating systems (see McCrea, D. A. and Rybak, L A., Organization of Mammalian Locomotor Rhythm and Pattern Generation, Brain Res. Rev., 2008, vol. 57, no. 1, p. 134), in which the rostral lumbar segments of the spinal cord play the role of a trigger of the locomotor function.

The frequency of stimulation is an important characteristic of the motor output. It was shown that step-like movements are evoked by stimulation frequencies in the range of 5-40 Hz. The amplitude of step-like movements induced by high-frequency stimulation (30-40 Hz) was usually higher than that of the movements induced by low frequency stimulation (5 Hz), although the duration of the stepping cycle varied slightly. The fact that a wide range of frequencies can effectively induce step-like movements is probably due to the functional state of the intact spinal cord and its pathways. For example, in spinal patients, the effective frequency range for the initiation of step-like movements using epidural stimulation was 30-40 Hz (according to Dimitrijevic, Gerasimenko, and Pinter, supra); in decerebrated cats, the frequency of 5 Hz was the most effective to elicit locomotion (according to our data) (see Gerasimenko, Roy, and Edgerton, supra).

The intensity of transcutaneous electrical stimulation (50-80 mA) that causes step-like movements is approximately 10 times higher than the intensity of the epidural stimulation initiating walking movements in spinal patients. See Dimitrijevic, Gerasimenko, and Pinter, supra. If we assume that the dorsal roots are the main target for both types of stimulation, we should agree that the current should be strong to activate them by transcutaneous electrical stimulation. Thus, we conclude that the location, frequency, and intensity of stimulation are the factors that determine the activation of the SN by tESCS.

The Origin of the Stepping Rhythm Evoked by tESCS

In most subjects, the involuntary step-like movements in the hip and knee joints were initiated by tESCS with a delay of 2-3 s after the start of stimulation. Typically, the amplitude of movements in the hip and knee joints increased smoothly and gradually with the subsequent involvement of the ankle joint (FIG. 9). A similar character of the initiation of involuntary step-like movements with gradual involvement of different motor pools of the leg muscles was also observed during the vibration of muscles (see Gurfinkel', Levik, Kazennikov, and Selionov, supra; Selionov, Ivanenko, Solopova, and Gurfinkel', supra; Gorodnichev, Machueva, Pivovarova, Semenov, Ivanov, Savokhin, Edgerton, and Gerasimenko, supra) and the epidural spinal cord stimulation. See Dimitrijevic, Gerasimenko, and Pinter, supra; Minassian, Persy, Rattay, Pinter, Kern, and Dimitrijevic, supra. This suggests that transcutaneous electrical stimulation, as well as the epidural stimulation, affects the SN through the activation of the dorsal root afferents entering the spinal cord. In addition to the dorsal roots and dorsal columns, the direct stimulation of the spinal cord may also activate the pyramidal and reticulospinal tracts, ventral roots, motor neurons, dorsal horn, and sympathetic tracts. See Barolat, G., Current Status of Epidural Spinal Cord Stimulation, *Neurosurg. Quart.,* 1995, vol. 5, no. 2, p. 98; Barolat, G., Epidural Spinal Cord Stimulation: Anatomical and Electrical Properties of the Intraspinal Structures Relevant To Spinal Cord Stimulation and Clinical Correlations, Neuromodul. Techn. Neur. Intelf-, 1998, vol. 1, no. 2, p. 63. During the tESCS, the electric current spreads perpendicular to the spinal column with a high density under the paravertebral electrode. See Troni, Bianco, Moja, and Dotta, supra. This stimulation apparently activates the dorsal roots immersed in the cerebrospinal fluid, but not the spinal cord neurons, which have a much lower conductivity. See Holsheimer, J., Computer Modeling of Spinal Cord Stimulation and Its Contribution to Therapeutic Efficacy, *Spinal Cord,* 1998, vol. 36, no. 8, p. 531. We assume that tESCS consequently involves in activity the afferents of groups Ia and Ib with the largest diameter and, thus, the lowest threshold, then the afferents of the group II, and the spinal interneurons mediating polysynaptic reflexes. The presence of polysynaptic components in the evoked potentials in the flexor muscles (FIG. 8) confirms that they participate in the SPG. Thus, we can say that tESCS activates different spinal neuronal systems; however, the dorsal roots with their mono and polysynaptic projections to the motor nuclei are the main ones among them. The contribution of mono and polysynaptic components in the formation of the stepping rhythm caused by tESCS is not known.

In our studies, single pulse stimulation resulted in monosynaptic reflexes in the majority of the leg muscles investigated. However, the electromyographic trains evoked by continuous tESCS that induced involuntary step-like movements were not formed by the amplitude modulation of monosynaptic reflexes, as it was in spinal rats and during the spinal epidural stimulation of patients. See Gerasimenko, Roy, and Edgerton, supra. Our data showed that the activity within electromyographic trains was not stimulus-dependent; i.e., EMG trains did not consist of separate reflex responses. Similar stimulus-independent EMG trains were observed during involuntary movements caused by spinal cord electromagnetic stimulation. See Gerasimenko, Gorodnichev, Machueva, Pivovarova, Semenov, Savochin, Roy, and Edgerton, supra; Gorodnichev, Machueva, Pivovarova, Semenov, Ivanov, Savokhin, Edgerton, and Gerasimenko, supra. In contrast, the step-like movements evoked by the epidural spinal stimulation in rats and spinal patients were stimulus-dependent. See Gerasimenko, Roy, and Edgerton, supra. In the extensor muscles, the EMG trains consisted mainly of monosynaptic reflexes; in the flexor muscles, polysynaptic reflexes dominated in the EMG trains. See Gerasimenko, Y. P., Ichiyama, R. M., Lavrov, L A., Courtine, G. Cai, L., Zhong, H., Roy, R. R., and Edgerton, V. R., Epidural Spinal Cord Stimulation Plus Quipazine Administration Enable Stepping in Complete Spinal Adult Rats, *J Neurophysiol.,* 2007, vol. 98, p. 2525; Minassian, K., Jilge, B., Rattay, F., Pinter, M. M., Binder, H., Gerstenbrand, F., and Dimitrijevic, M. R., Stepping-Like Movements in Humans with Complete Spinal Cord Injury Induced by Epidural Stimulation of the Lumbar Cord: Electromyographic Study of Compound Muscle Action Potentials, *Spinal Cord* 2004, vol. 42, p. 401. It is not clear why single cutaneous and, respectively, single epidural spinal cord stimulation causes the same monosynaptic reflexes in healthy subjects and spinal patients; however, continuous stimulation elicits their step-like movements through different mechanisms. We assume that, in healthy subjects, tESCS increases the excitability of the neuronal locomotor network, being a trigger for its activation, in the same way as in the case of vibration-induced step-like movements. See Selionov, Ivanenko, Solopova, and Gurfinkel', supra. However, we need additional studies to understand in detail how the tESCS elicits involuntary step-like movements.

In this study, a new noninvasive access to locomotor spinal neural networks in humans by means of tESCS has been described. A special design of the stimulator, which generated bipolar pulses filled with high-frequency carrier, allowed us to stimulate the spinal cord relatively painlessly and elicit involuntary step-like movements. The fundamental importance of our study consists in the new data in favor of the existence of SN in humans that can coordinate stepping patterns and the evidence of the possibility to engage this SN using noninvasive effects on the structures of the spinal cord. This increases prospects for widespread use of transcutaneous techniques in electrical spinal cord stimulation to study the mechanisms underlying the regulation of the locomotor behavior in healthy subjects and for the rehabilitation and motor recovery of patients after spinal cord injuries and after other neuromotor dysfunctions.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention is claimed as follows:

1. A neuromodulation system for inducing locomotor activity in a mammal, the neuromodulation system comprising:
   a processor;
   a signal generator communicatively coupled to the processor;
   at least one electromyography electrode communicatively coupled to the processor;
   at least two electrodes electrically coupled to the signal generator; and a memory device communicatively coupled to the processor and configured to store instructions, which when executed by the processor, cause the processor, in cooperation with the signal generator and the at least two electrodes, to deliver a continuous therapeutic signal having parameter values including a 0.5 Hz to 100 Hz waveform with an overlapping high frequency pulse at 5 kHz to 10 kHz delivered at 30-200 mA to the mammal, wherein the at least one electromyography electrode measures a response related to delivery of the continuous therapeutic signal to the mammal, and wherein the processor is configured to synchronize the parameter values of the continuous therapeutic signal with the response measured by the at least one electromyography electrode and store to the memory the synchronization for selection of new parameter values to deliver a subsequent continuous therapeutic signal.

2. The neuromodulation system of claim 1, wherein the continuous therapeutic signal is delivered by the at least two electrodes to a human.

3. The neuromodulation system of claim 1, wherein the signal generator is configured to deliver the continuous therapeutic signal at 85-100 mA.

4. The neuromodulation system of claim 1, wherein the signal generator is configured to deliver the overlapping high frequency pulse by providing a 10 kHz pulse.

5. The neuromodulation system of claim 1, wherein the signal generator is configured to deliver the overlapping high frequency pulse by providing a 5 kHz pulse.

6. The neuromodulation system of claim 1, wherein the continuous therapeutic signal is delivered by the at least two electrodes paraspinally over a neck of the mammal.

7. The neuromodulation system of claim 6, wherein the neck of the mammal includes a cervical portion of a spinal cord and a brainstem.

8. The neuromodulation system of claim 1, wherein the signal generator is configured to deliver the continuous therapeutic signal paraspinally over a lower back of the mammal.

9. The neuromodulation system of claim 8, wherein the lower back includes at least one of a lumbar portion, a lumbosacral portion, and a sacral portion of the spinal cord.

10. The neuromodulation system of claim 1, wherein the signal generator is configured to deliver the continuous therapeutic signal to a thoracic portion of a spinal cord or to an end organ.

11. The neuromodulation system of claim 10, wherein the thoracic portion of the spinal cord includes T11-T12 vertebrae.

12. The neuromodulation system of claim 1, wherein the neuromodulation system is configured to treat the mammal for a spinal cord injury which is classified as one of motor complete and motor incomplete.

13. The neuromodulation system of claim 1, wherein the neuromodulation system is configured to treat the mammal for an ischemic brain injury which is an injury from at least one of a stroke and acute trauma, has a neurodegenerative brain injury, or a combination thereof.

14. The neuromodulation system of claim 13, wherein the neurodegenerative brain injury is a brain injury associated with a condition selected from the group consisting of Parkinson's disease, Huntington's disease, Alzheimer's disease, ischemia, stroke, amyotrophic lateral sclerosis (ALS), primary lateral sclerosis (PLS) or other neurological disorders such as cerebral palsy.

15. The neuromodulation system of claim 1, wherein the neuromodulatoin system is used to treat chronic pain, spasm, autonomic function, sexual function, vasomotor function, or cognitive function.

16. The neuromodulation system of claim 1, wherein the system induces motor activity which comprises at least one of standing, stepping, a walking motor pattern, sitting down, laying down, reaching, grasping, pulling, chewing, swallowing, sexual function, respiratory function, and pushing.

17. The neuromodulation system of claim 1, wherein the continuous therapeutic signal and the overlapping high frequency pulse are square waves, and wherein the continuous therapeutic signal and the overlapping high frequency pulse have unequal parameter values.

18. A neuromodulation system comprising:
a processor;
a first signal generator communicatively coupled to the processor;
a second signal generator communicatively coupled to the processor;
at least one electromyography electrode communicatively coupled to the processor;
at least two electrodes electrically coupled to at least one of the first signal generator and the second signal generator; and
a memory device communicatively coupled to the processor and configured to store instructions, which when executed by the processor, cause the processor, in cooperation with the first signal generator, the second signal generator, and the at least two electrodes, to deliver a secondary high frequency electric pulse having a first parameter value of 10 kHz, which overlaps with a continuous therapeutic primary biphasic low frequency pulse delivered having a second parameter value of 0.5 Hz to 100 Hz resulting in less skin impedance and pain free stimulation, wherein the continuous therapeutic primary biphasic low frequency pulse is delivered at a third parameter value of 30-200 mA, wherein the at least one electromyography electrode measures a response related to delivery of the continuous therapeutic primary biphasic low frequency pulse and the secondary high frequency electric pulse to the mammal, and wherein the processor is configured to synchronize the parameter values of the secondary high frequency electric pulse and the continuous therapeutic primary biphasic low frequency pulse with the response measured by the at least one electromyography electrode and store to the memory the synchronization for selection of new parameter values to deliver at least one of a subsequent primary biphasic low frequency pulse and a subsequent secondary high frequency electric pulse.

19. The neuromodulation system of claim 18, wherein the processor, in cooperation with the first signal generator and the second signal generator is configured to deliver the continuous therapeutic primary biphasic low frequency pulse at 5-40 Hz.

20. The neuromodulation system of claim 18, wherein the processor, in cooperation with the first signal generator and the second signal generator is configured to deliver the secondary high frequency electric pulse paraspinally.

* * * * *